United States Patent
Seitz et al.

(10) Patent No.: US 11,712,375 B2
(45) Date of Patent: *Aug. 1, 2023

(54) ADULT ABSORBENT ARTICLES AND ARRAYS THEREOF

(71) Applicant: The Procter & Gamble Company, Cincinnati, OH (US)

(72) Inventors: Bret Darren Seitz, West Chester, OH (US); Douglas Gregory Stevens, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 347 days.

This patent is subject to a terminal disclaimer.

(21) Appl. No.: 16/933,141

(22) Filed: Jul. 20, 2020

(65) Prior Publication Data
US 2020/0345560 A1 Nov. 5, 2020

Related U.S. Application Data

(63) Continuation of application No. 14/670,483, filed on Mar. 27, 2015, now Pat. No. 10,751,226.
(Continued)

(51) Int. Cl.
*A61F 13/47* (2006.01)
*A61F 13/472* (2006.01)
(Continued)

(52) U.S. Cl.
CPC ........ *A61F 13/47* (2013.01); *A61F 13/47218* (2013.01); *A61F 13/551* (2013.01); *A61F 2013/15373* (2013.01)

(58) Field of Classification Search
CPC .. A61F 13/47; A61F 13/47218; A61F 13/551; A61F 2013/15373
See application file for complete search history.

(56) References Cited

U.S. PATENT DOCUMENTS 3,926,189 A  12/1975 Taylor
4,037,602 A   7/1977 Hawthorne
(Continued)

FOREIGN PATENT DOCUMENTS

EP      2054001 B1    5/2013
JP     2005177160 A   7/2005
(Continued)

OTHER PUBLICATIONS

Extended European Search Report and Search Opinion; Application Ser. No. 19205529.1; dated Nov. 27, 2019; 8 pages.
(Continued)

*Primary Examiner* — Michele M Kidwell
(74) *Attorney, Agent, or Firm* — William E. Gallagher; George H. Leal

(57) ABSTRACT

An array of absorbent articles each having a topsheet, a backsheet, and an absorbent core is described. A first absorbent article has a first physical feature disposed between the topsheet and the absorbent core, and a second absorbent article has a second physical feature disposed between the topsheet and the absorbent core. The first physical feature has a first length between 27 and 77 percent of a first absorbent core length. The second physical feature has a second length between 27 and 77 percent of a second absorbent core length. The first length is less than the second length, and the first physical feature comprises a convex portion oriented toward a first end of the first absorbent article and/or the second physical feature comprises a convex portion oriented toward a first end of the second absorbent article.

21 Claims, 19 Drawing Sheets

Related U.S. Application Data

(60) Provisional application No. 61/971,801, filed on Mar. 28, 2014.

(51) Int. Cl.
*A61F 13/15* (2006.01)
*A61F 13/551* (2006.01)

(56) References Cited

U.S. PATENT DOCUMENTS

| | | |
|---|---|---|
| 4,585,448 A | 4/1986 | Enloe |
| 4,950,264 A | 8/1990 | Osborn, III |
| 5,460,623 A | 10/1995 | Emenaker |
| 5,569,231 A | 10/1996 | Emenaker et al. |
| 5,839,585 A | 11/1998 | Miller |
| 5,897,542 A | 4/1999 | Lash et al. |
| 6,090,090 A | 7/2000 | Roe et al. |
| 6,093,027 A | 7/2000 | Unger et al. |
| 6,229,061 B1 | 5/2001 | Dragoo |
| 6,311,403 B1 | 11/2001 | Macrini |
| 6,488,202 B1 | 12/2002 | Seitz et al. |
| 6,604,609 B2 | 8/2003 | Bruce et al. |
| 6,648,864 B2 | 11/2003 | Ronn et al. |
| 6,711,455 B1 | 3/2004 | Holloway et al. |
| 6,810,300 B1 | 10/2004 | Woltman et al. |
| 6,884,238 B2 | 4/2005 | Underhill et al. |
| 7,222,732 B2 | 5/2007 | Ronn et al. |
| 7,641,641 B2 | 1/2010 | Ramshak |
| 8,273,067 B2 | 9/2012 | Cohen |
| 8,378,165 B2 | 2/2013 | Visscher et al. |
| 8,386,326 B2 | 2/2013 | Woltman et al. |
| 8,478,663 B2 | 7/2013 | Lu et al. |
| 8,545,471 B2 | 10/2013 | Ashton et al. |
| 8,548,875 B2 | 10/2013 | Woltman et al. |
| 2003/0055393 A1 | 3/2003 | Stults et al. |
| 2003/0226266 A1 | 12/2003 | Ellis |
| 2004/0122745 A1 | 6/2004 | Hantke et al. |
| 2006/0069372 A1 | 3/2006 | Chakravarty |
| 2008/0051749 A1 | 2/2008 | Betts et al. |
| 2008/0110782 A1 | 5/2008 | Burgdorf |
| 2008/0110984 A1 | 5/2008 | Uchitani |
| 2008/0128308 A1 | 6/2008 | Betts |
| 2009/0247815 A1 | 10/2009 | Hou et al. |
| 2009/0264851 A1 | 10/2009 | Richlen et al. |
| 2009/0266733 A1 | 10/2009 | Betts |
| 2011/0028929 A1 | 2/2011 | Hopkins |
| 2011/0137624 A1 | 6/2011 | Weisman et al. |
| 2013/0135475 A1 | 5/2013 | Stam et al. |
| 2013/0152847 A1 | 6/2013 | Setoodeh et al. |
| 2015/0272787 A1 | 10/2015 | Seitz |

FOREIGN PATENT DOCUMENTS

| | | |
|---|---|---|
| JP | 2009090704 A | 4/2009 |
| WO | 9629037 A1 | 9/1996 |
| WO | 9739713 A1 | 10/1997 |
| WO | 2007073254 A1 | 6/2007 |
| WO | 2009128029 A2 | 10/2009 |

OTHER PUBLICATIONS

International Search Report and Written Opinion; Application Ser. No. PCT/US2015/022903; dated Jun. 18, 2015; 11 pages.

All Office Actions for U.S. Appl. No. 14/670,483, filed Mar. 27, 2015.

ADULT ABSORBENT ARTICLES AND ARRAYS THEREOF

FIELD OF THE INVENTION

The present invention is directed to an array of adult absorbent articles which are designed for different body types, as well as to methods for making and packaging a plurality of absorbent articles. The adult absorbent articles are generally designed and configured to manage bodily exudates such as urine, menses, or other vaginal discharges. Exemplary adult absorbent articles include sanitary napkins (aka pads) and pantiliners and incontinence pads, pants, and liners.

BACKGROUND OF THE INVENTION

Menstrual fluid and urine have different fluid insult physio-chemical properties (e.g., viscosity, fluid dynamics, etc.), volumes, and absorption rates. For example, menstrual flow typically consists of two patterns. The first pattern is "trickle" flow, which varies from 0.1 to 2 ml per hour. The second pattern is "gush" flow which varies from 2-3 ml but can be up to 5 ml. Typical gush rates are from ~0.5-2 ml/sec. Gush flow can result from an accumulation of menses pooling in the vagina which may then exit the body upon a change in position, such as a transition from sitting to standing. For consumers who suffer from urinary incontinence, urine voiding consists of two general types: stress urinary incontinence (SUI) and urge urinary incontinence (UUI). SUI is caused by high pressure on the bladder induced by coughing, sneezing, laughing, bending, etc., and can result in a high flow rate though at a smaller urine volume that that associated with UUI. UUI can result in a full bladder release, though at a lower flow rate than that associated with SUI. Spreading occurs when fluid moves along the body or when fluid is trapped in the interface between the wearer's body and the adult absorbent article. This can be uncomfortable for a wearer, can lead to feelings of uncleanliness and insecurity, or lead to embarrassing leaks. There is a desire to minimize spreading of urine or menstrual fluid.

Desirably, an adult absorbent article should maintain contact with and conform as closely as possible to a wearer's body. Such a body-conforming capability may increase the effectiveness of the adult absorbent article by reducing the possibility that menses, urine, or the like will spread, or travel along the wearer's body rather than into the adult absorbent. However, adult absorbent articles on the market do not address body shape or size or close fit beyond a choice of two or three lengths. Available adult absorbent articles are generally designed and marketed based upon the absorbency level of the product (e.g., light liner, regular pad, heavy pad), features (e.g., wings or no wings, regular or long length, scented or unscented) or the time of day or length of time the product is expected to be used (e.g., overnight pads). There is a need for adult absorbent articles which conform well to various wearers' bodies. There is a need for adult absorbent articles which provide a close fit such that spreading of urine and/or menstrual fluid is reduced or eliminated. While there is a wide range of body shapes and sizes among women, available products do not reflect this wide range; rather, absorbent articles available today follow a one-size-fits-all (or even one-size-fits-small) approach. Yet, body mass index (BMI) is on the rise globally for both men and women. In the U.S. alone, more than ⅓ of adult females are now considered obese (BMI>30). This has changed significantly over the past 30 years; in 1980 only about 16% of U.S. adult females were obese. Today's absorbent articles struggle to deliver superior protection for larger women (relative to smaller women). There is a lack of recognition and understanding of this issue by adult absorbent article manufacturers. Accordingly, there is a need to develop adult absorbent articles for a variety body shapes such that there is improved contact between skin and the adult absorbent article to reduce the occurrence of spreading. There is a need for adult absorbent articles which are designed for wearers based on their BMI. There is a need to communicate to wearers the benefits of such customized adult absorbent articles in an easy-to-understand manner (e.g., some women may not understand what BMI is or know their BMI number) which is not off-putting (e.g., without stigmatizing or embarrassing women based on their BMI).

These are all objects of the present invention; embodiments of the present invention may combine various objects mentioned. A particular embodiment may, but need not, embody every object of the invention.

SUMMARY OF THE INVENTION

The present invention is directed to arrays of absorbent articles. In accordance with one exemplary embodiment, an adult absorbent article comprises a topsheet, a backsheet, and an absorbent core; the absorbent article comprises a physical feature to at least partially fill a wearer's panty-body void; wherein the wearer has a BMI greater than about 25.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION OF THE INVENTION

Figure 1A:
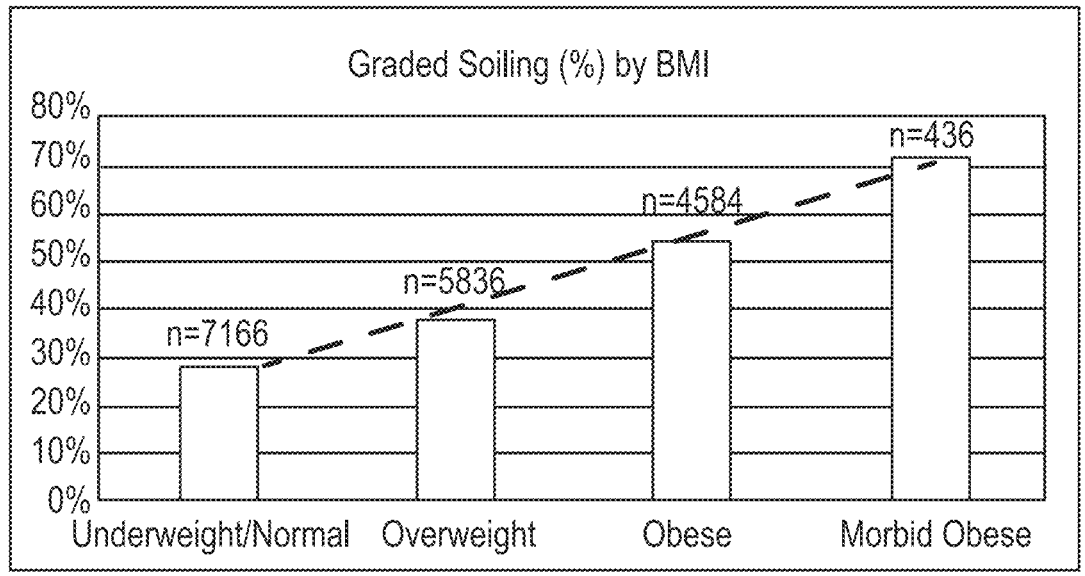
FIGS. 1A-1C are charts illustrating soiling as a function of BMI and panty size.

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims).

No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112 f.

"Array" means a display of packages comprising disposable articles of different sizes having like article constructions (e.g., same elastomeric materials [compositionally and/or structurally] in the flaps, graphic elements) said packages having the same brand and/or sub-brand, and said packages oriented in proximity to each other in a given area of a retail store. An array is marketed as a line-up of products normally having like packaging elements (e.g., packaging material type, film, paper, dominant color, design theme, etc.) that convey to consumers that the different individual packages are part of a larger line-up. Arrays often have the same brand, for example, "Depend," and same sub-brand, for example, "for Women Underwear." A different array may have the brand "Depend" and the sub-brand "Silhouette For Women." The differences between the "for Women Underwear" array and the "Silhouette For Women" arrays include different elastomeric materials in the side flaps, where "for Women Underwear" comprises strands as the elastomeric material and "Silhouette For Women" comprises a film elastomeric material." Furthermore, the packaging is distinctly different in that "for Women Underwear" is packaged in a predominately green, film bag and "Silhouette For Women" is packaged in a predominately maroon box.

Further regarding "Arrays," as another example of two separate "arrays" having the same brand, "Certainty," one line-up has the sub-brand "Women's Underwear." A different array may have the same brand "Certainty" and the sub-brand "Smooth Shape Briefs for Women." The differences between the "Women's Underwear" array and the "Smooth Shape Briefs for Women" arrays include different elastomeric materials in the side flaps, where "Women's Underwear" comprises strands as the elastomeric material and "Smooth Shape Briefs for Women" comprises a film elastomeric material." Furthermore, the packaging is distinctly different in that "Women's Underwear" is packaged in a predominately blue, film bag and "Smooth Shape Briefs for Women" is packaged in a predominately maroon box.

Arrays also often have the same trademarks, including trademarks of the brand, sub-brand, and/or features and/or benefits across the line-up.

"On-line Array" means an "Array" distributed by a common on-line source.

The body mass index (BMI) is a classification system for body shapes based upon height and mass. BMI may be calculated as follows:

$$BMI = \frac{\text{weight (kg)}}{\text{height (m)}^2} = \frac{703 * \text{weight (lb)}}{\text{height (in)}^2}$$

It is also common to determine BMI based upon a chart of height verses weight, see for example, FIG. 1. The index comprises different classes of body mass, including: underweight (BMI<20), normal weight (BMI 20-25), overweight (BMI 25-30), obese (BMI 30-40), and morbidly obese (BMI>40).

"Coronal plane" as used herein, describes a vertical plane which extends through a standing female body dividing said body into anterior and posterior portions, and said coronal plane extending through the shoulder and vaginal opening, bisecting vaginal opening into anterior and posterior portions.

"Sagittal plane" as used herein describes a plane which extends through the body of a standing wearer and bisects the body of the standing wearer into left and right halves.

"Thigh Spacing" means the narrowest lateral distance between the thighs (inner portions of the thigh 1100A and 1100B) while the person whose thighs are being measured is in the neutral position with their feet approximately shoulder width apart. The lateral distance being parallel to the coronal plane and being on a transverse plane. The transverse plane being perpendicular to the coronal plane and extending through the Gluteal Sulcus (the gluteal sulcus is often referred to as the fold of the buttock or the gluteal fold of the horizontal gluteal crease). This is illustrated in FIG. 2 and in FIG. 3 at plane B:B of FIG. 2.

Figure 2:
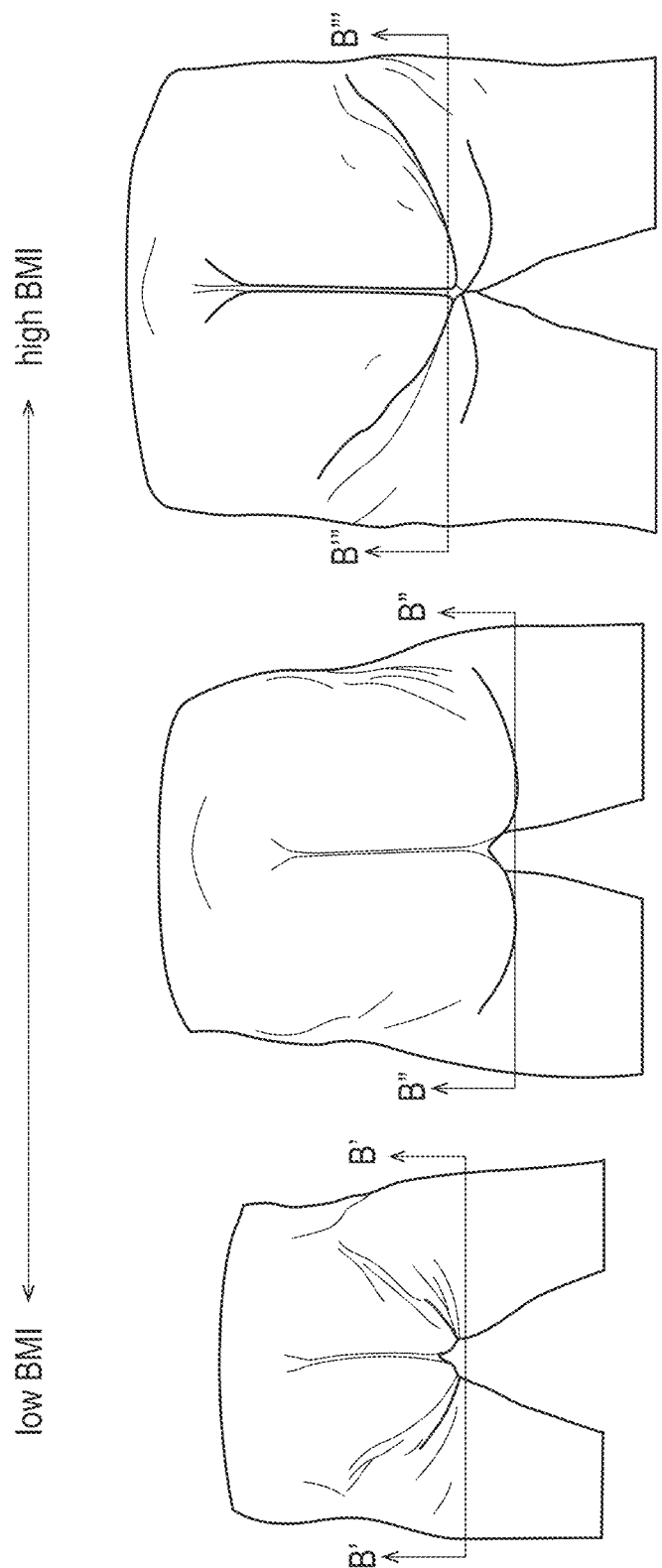
FIG. 2 shows representative female body shapes of differing BMI where the transverse plane B:B is determined at the gluteal sulcus.
Figure 3:
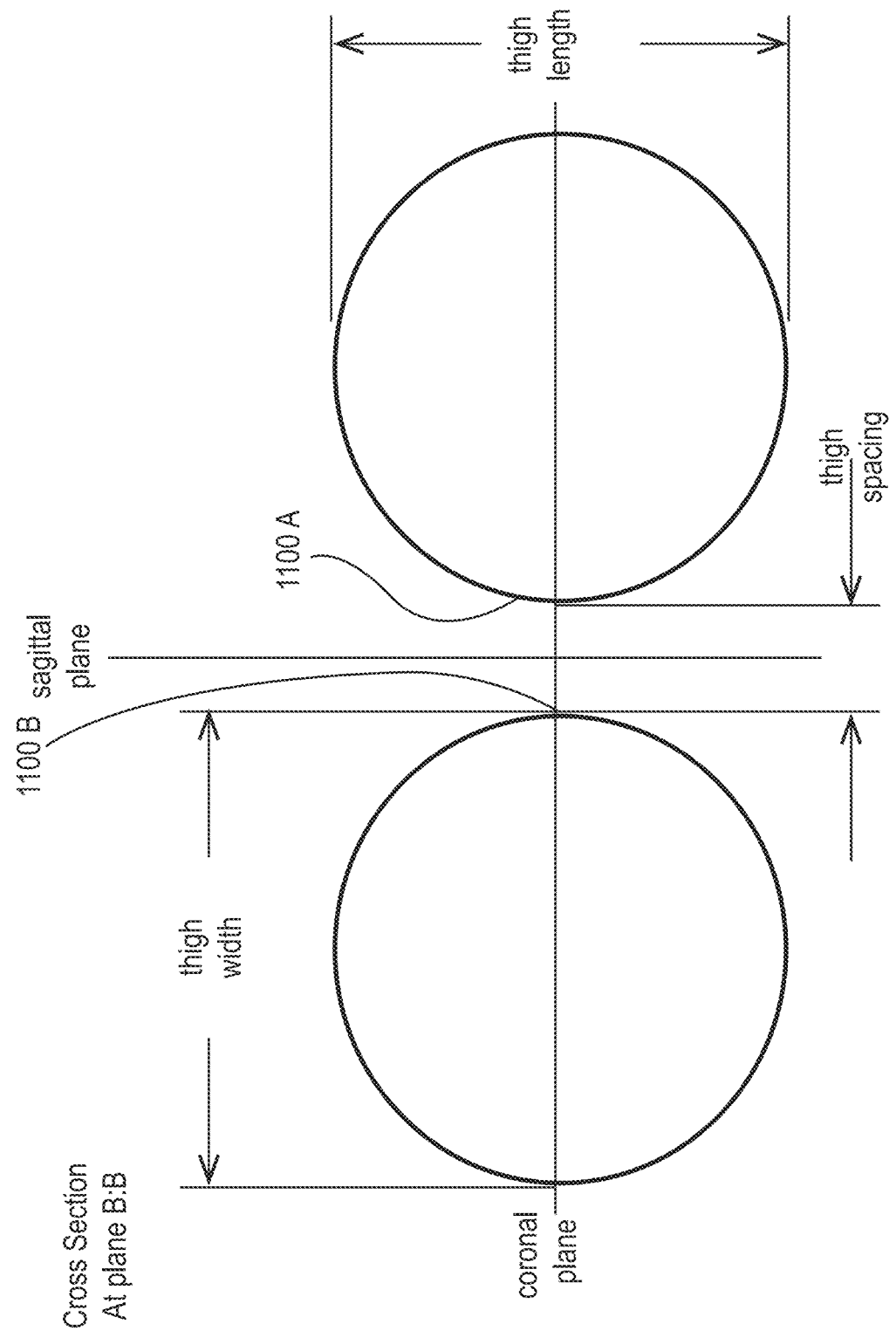
FIG. 3 shows representative female morphological measurements taken at plane B:B of FIG. 2, including thigh spacing, thigh diameter parallel to the sagittal plane (thigh length), and thigh diameter parallel to the coronal plane (thigh width).

"Thigh Eccentricity" is the approximate eccentricity of the thigh at plane B:B of FIG. 2, where plane B:B is described above. Hereafter, Thigh Eccentricity is considered negative when the major axis of the thigh cross section at plane B:B is perpendicular to the coronal plane of the body. The thigh's major axis is the larger of either the Thigh Width, or Thigh Length as illustrated in FIG. 3.

"Thigh" means the circumference of the thigh at its juncture with the buttock, the measurement made perpendicular to the long axis of the thigh.

Figure 1B:
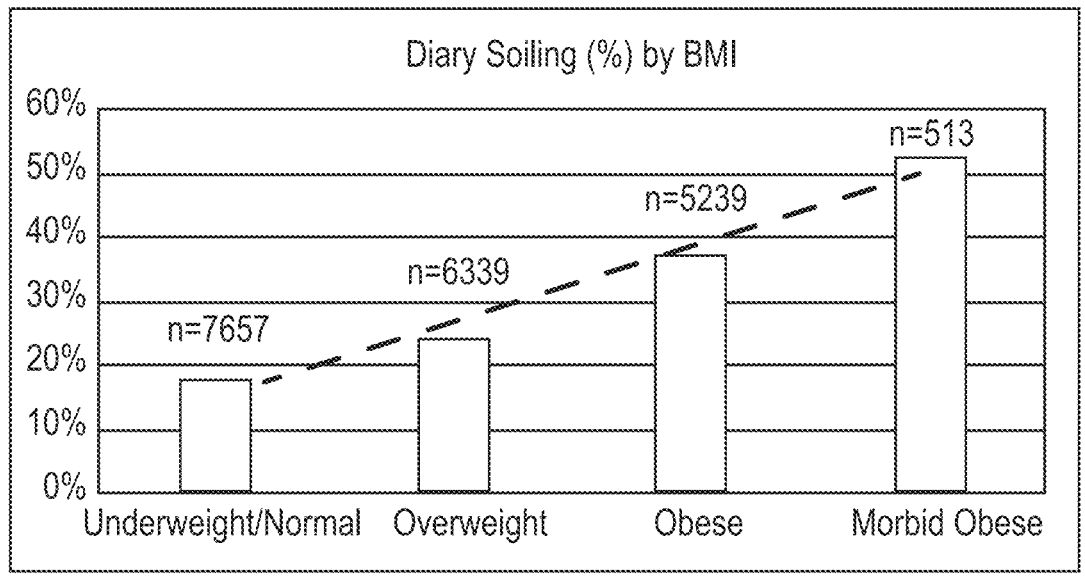
Figure 1C:
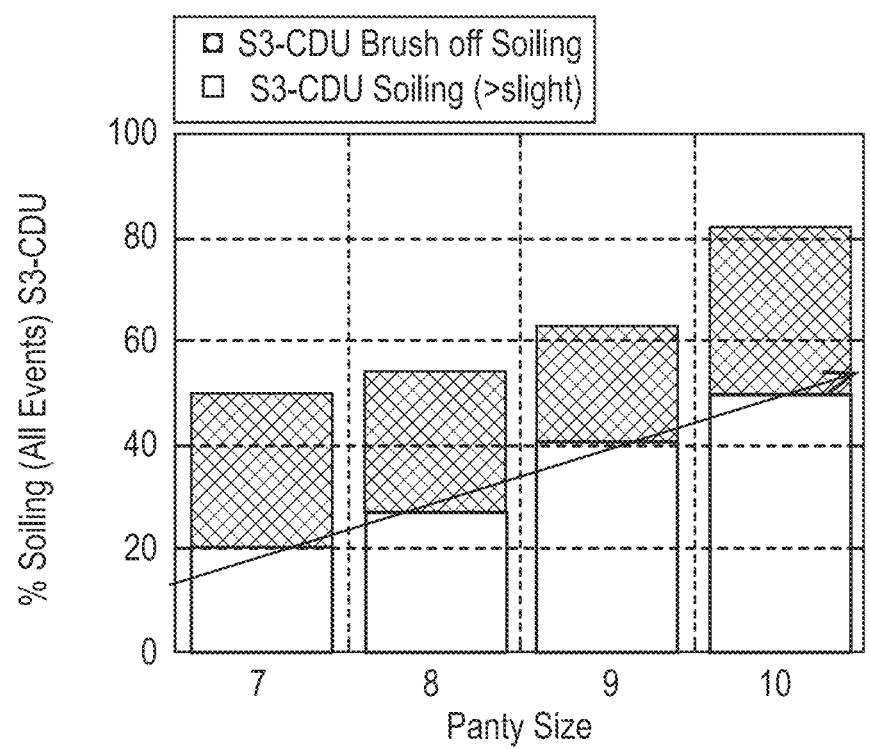

As stated previously, BMI is on the rise globally for both men & women. The inventors have discovered how the general female body shape changes as BMI increases. It has also been found that currently marketed adult absorbent articles struggle to deliver superior protection for the higher BMI wearers (relative to the lower BMI wearers). As BMI increases and body shape changes, it was discovered that the shape/morphology of the intimate region through the crotch also changes. Several performance related metrics, e.g., panty-soiling and fluid left on the body (amount and coverage area) all tend to increase as BMI and panty size increases, as illustrated in FIGS. 1A, 1B, and 1C. The increase in these performance outages is not due to an increase in fluid discharge, since menstrual flow is not correlated to body size and weight. Rather, performance outages are independent of the load in the sanitary napkin (a larger woman will be at a performance disadvantage versus a smaller woman for the same amount of fluid in the pad). The probability of a consumer suffering from urinary incontinence can, however, be linked to BMI (among other factors, such as age, number of childbirths, menopause, injuries, etc.).

It may be argued that today's adult absorbent articles address these performance outages inherently via varying surface areas and absorbencies among products. For instance, subsequently larger sizes within today's product arrays are essentially up-scaled versions of the smaller sizes (i.e., size scaling—increase in L1, increase in W1, or increase in both L1 and W1 (shown in FIG. 15B)). However, it has been found that these are not the best ways to address performance outages stemming from a higher BMI. A mechanistic understanding of why higher BMI women experience these performance outages at a greater rate than lower BMI women is essential in establishing the product requirements and designs necessary to deliver the same or even better performance for the higher BMI population. The need for this mechanistic understanding of BMI has not been recognized until now.

Figure 4:
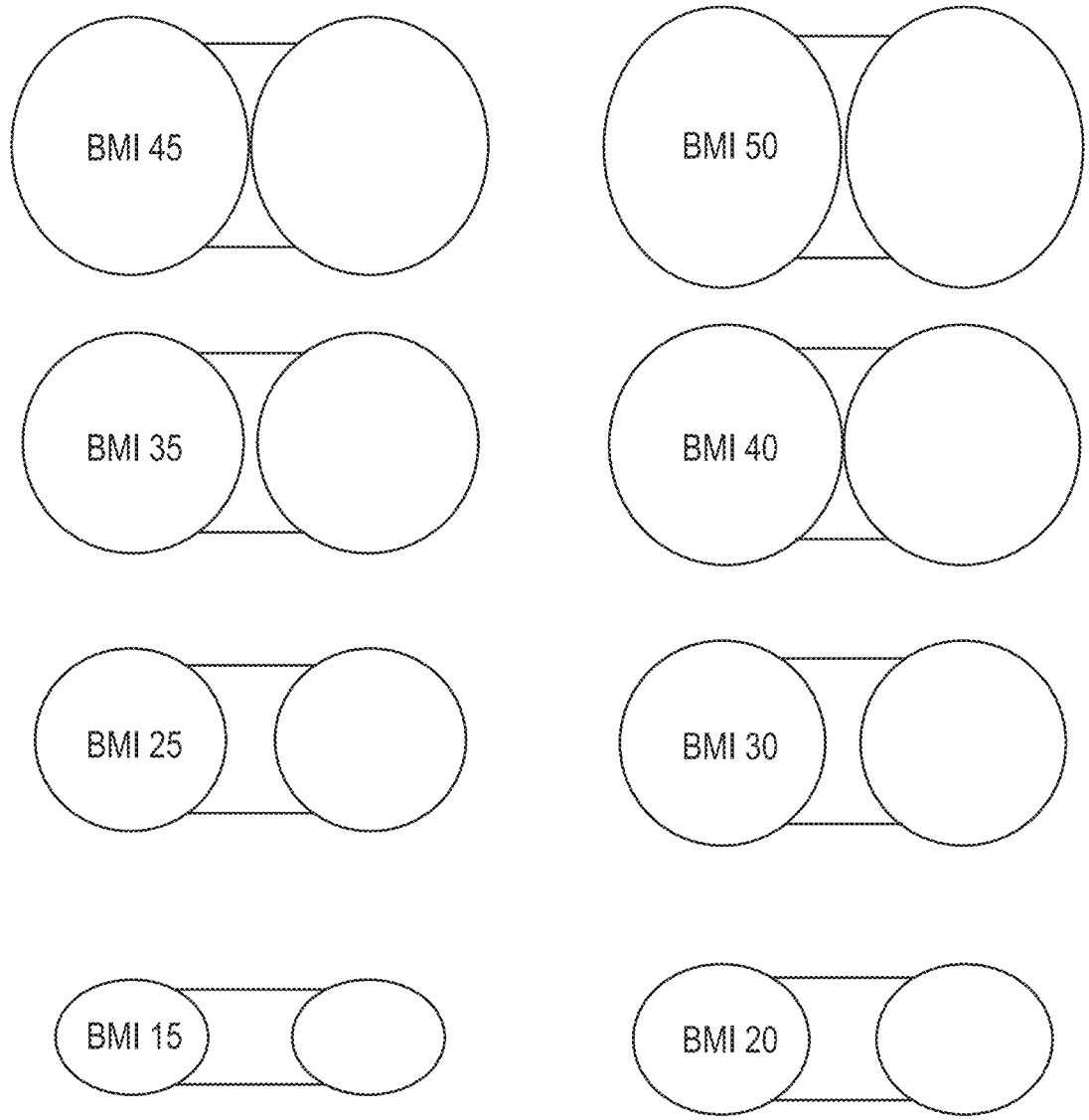
FIG. 4 shows the average female morphological shapes at plane B:B of FIG. 2 as a function of BMI.
Figure 5:
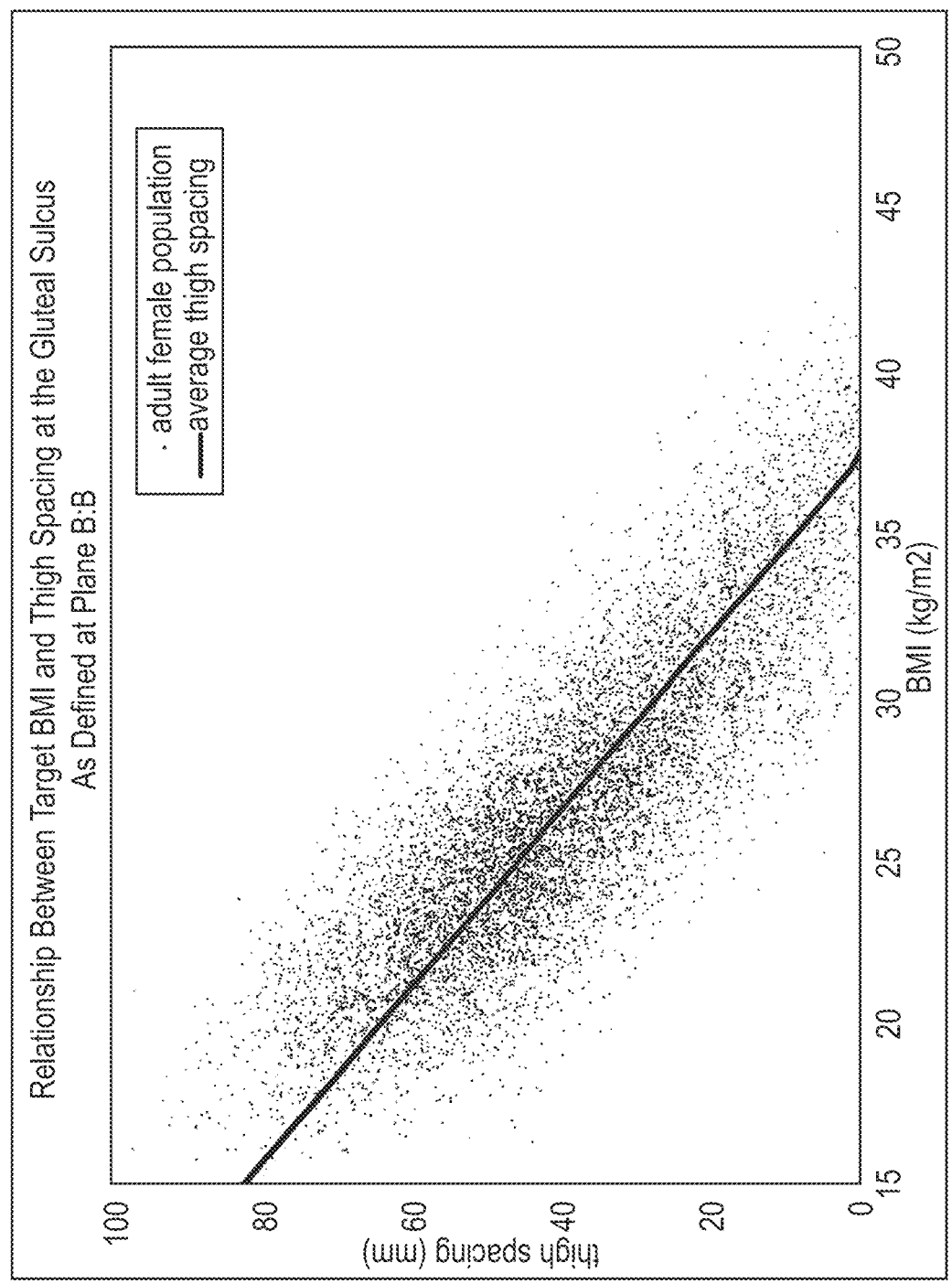
FIG. 5 is a chart showing the relationship between Target BMI and Thigh Spacing at plane B:B of FIG. 2.
Figure 6:
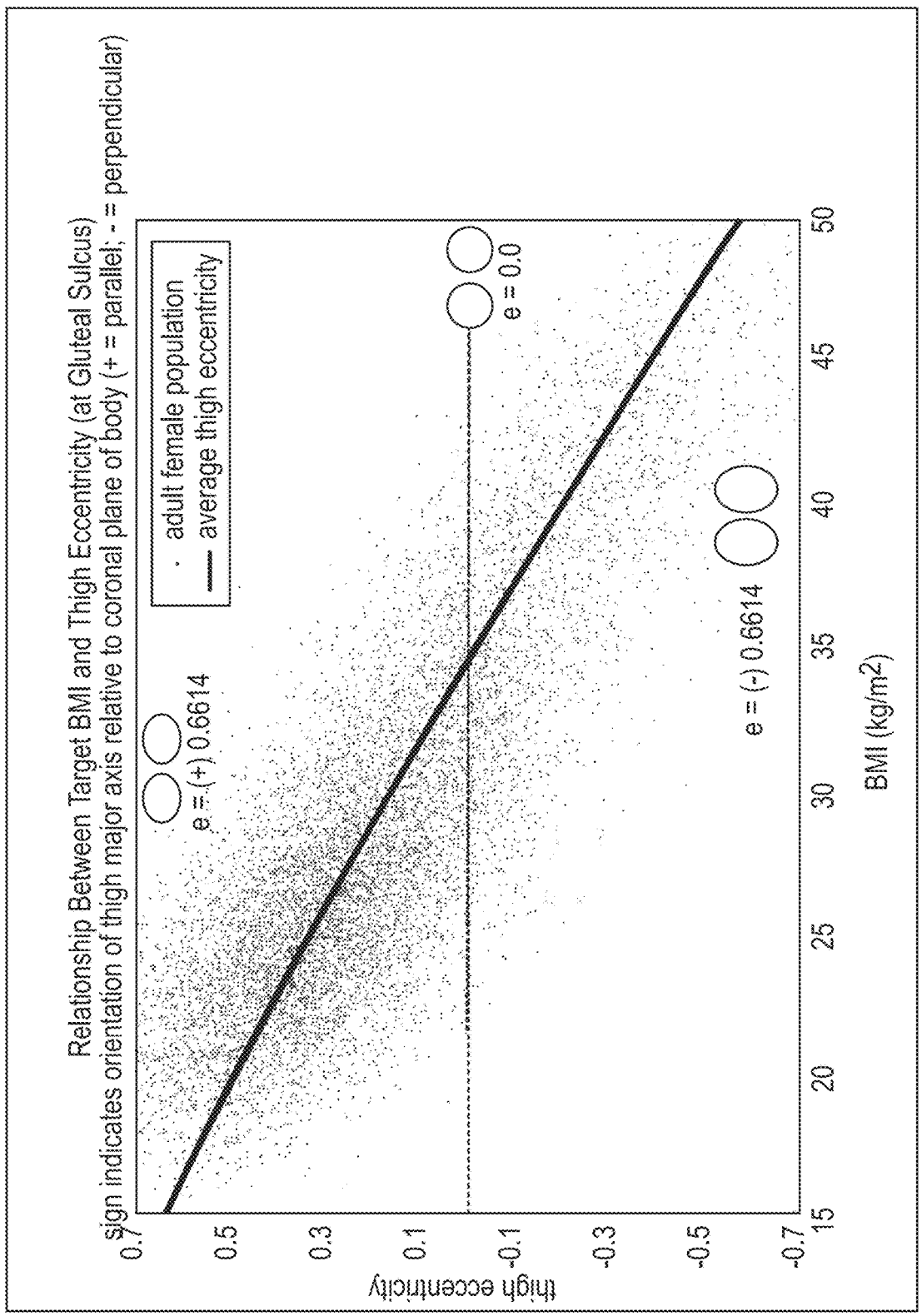
FIG. 6 is a chart showing the relationship between Target BMI and Thigh Eccentricity at plane B:B of FIG. 2.
Figure 7:
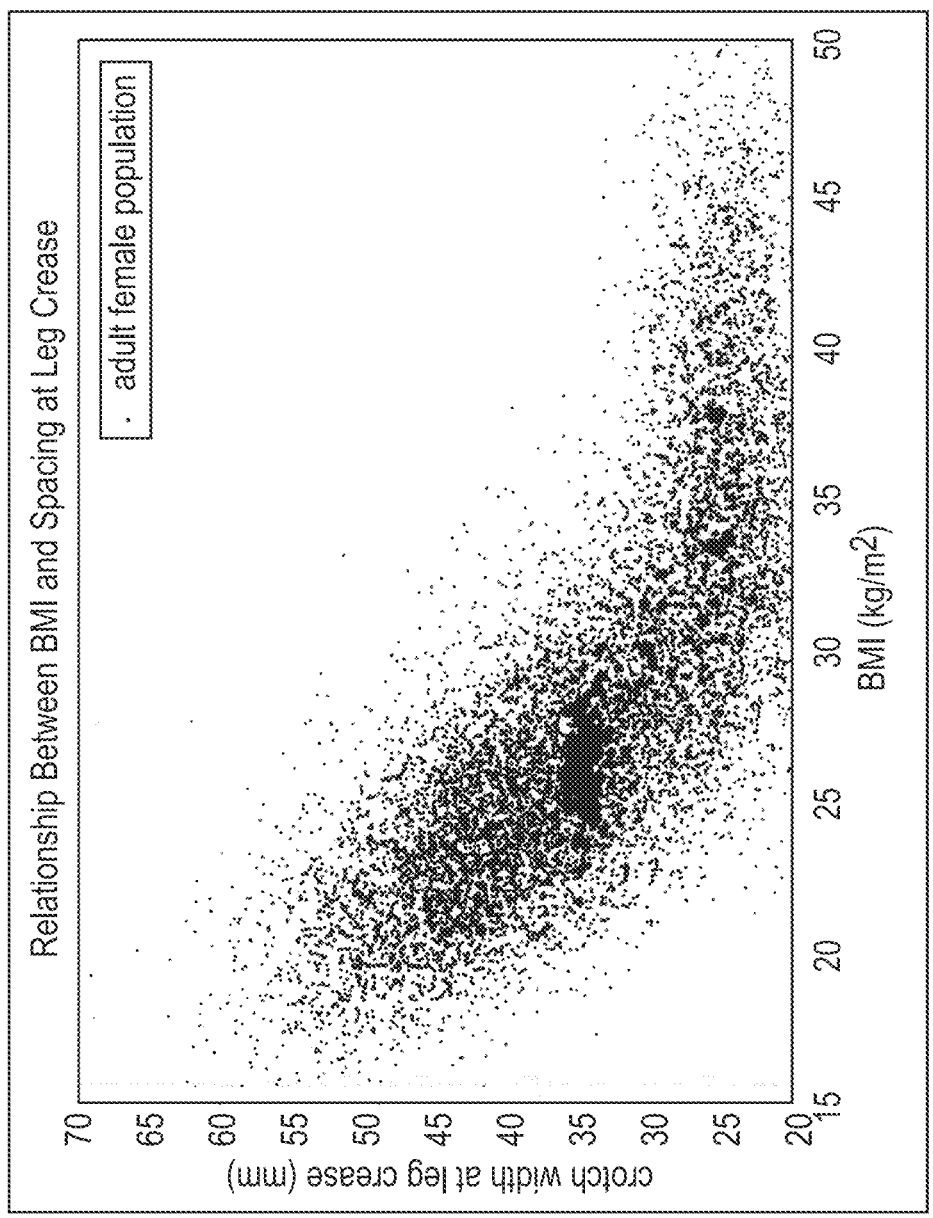
FIG. 7 is a chart showing the relationship between BMI and spacing between the thighs at the intersection of the thighs with the torso.

There are several mechanistic explanations as to why product performance degrades as BMI increases. For instance, there exists a higher probability of fat folds/skin creases in higher BMI women which can attract the fluid (capillarity) and trap it once there. Additionally, there is a higher probability of reduced space between the thighs for higher BMI women, specifically at the crotch where a pad sits in a panty. The reduced spacing is illustrated in FIGS. 2-4, and in the charts of FIGS. 5 and 6. As BMI increases, the spacing between the thighs at the Gluteal Sulcus—hereafter, "thigh (gluteal sulcus) spacing"—decreases. Additionally, as BMI increases, the eccentricity of the thigh at the Gluteal Sulcus changes as is illustrated in FIG. 4 and in the chart of FIG. 6. This change results in a larger radius (smaller curvature) and a longer thigh axis (perpendicular to the coronal plane of the body). Additionally, the spacing between the thighs (at the intersection of the inner thighs 1100A and 1100B with the torso)—hereafter, "thigh (torso) spacing"—decreases as BMI increases as depicted in FIG. 7. The decrease in thigh (torso) spacing occurs with increasing BMI until a BMI of about 30 is reached. For BMI values above 30, the thigh (torso) spacing flattens out.

Figure 8B:
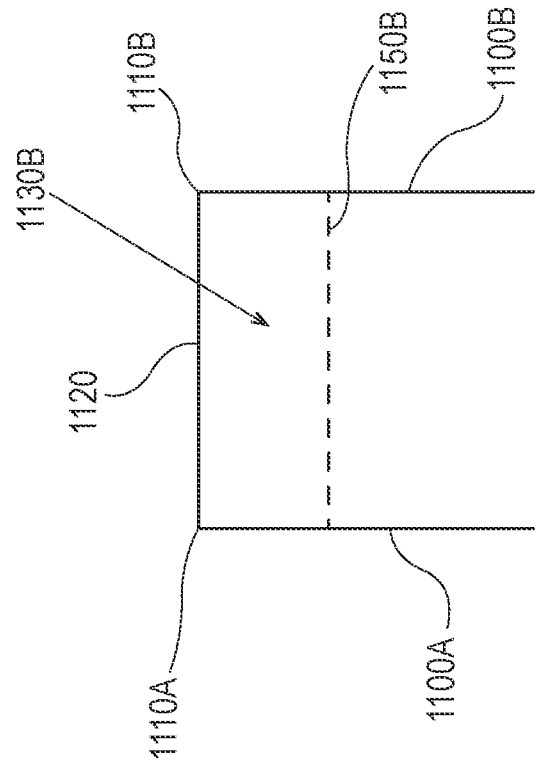
FIG. 8B shows an approximation of the open area of the crotch on the coronal plane defined at the location where inner thighs intersect the torso and the gluteal sulcus for a low BMI value, e.g. 15.
Figure 8A:
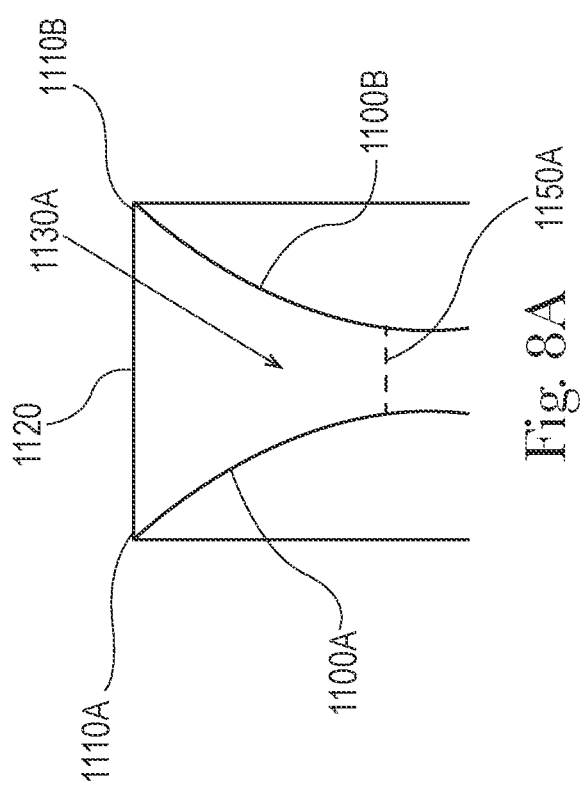
FIG. 8A shows an approximation of the open area of the crotch on the coronal plane, defined at the location where inner thighs 1100A and 1100B intersect the torso 1120 and the gluteal sulcus for a high BMI value, e.g. 35.
Figure 9A:
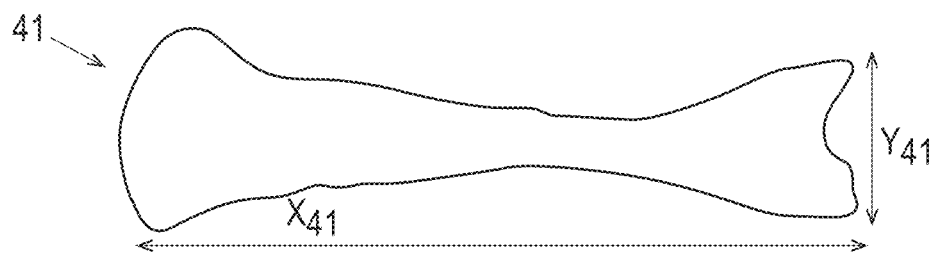
FIG. 9A shows a top view of a deformed feminine hygiene pad worn by a 34 BMI consumer.
Figure 9B:
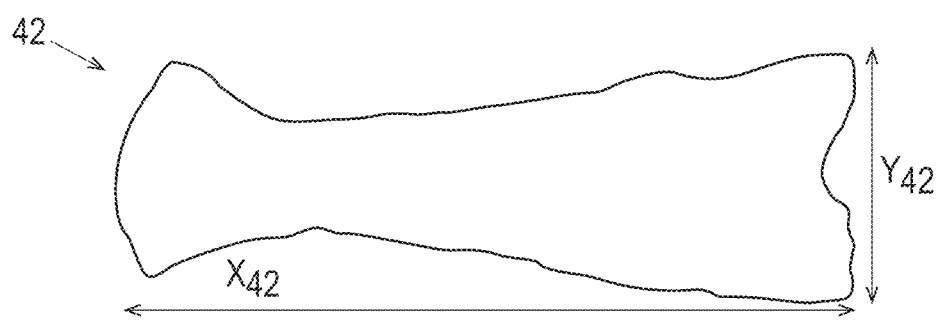
FIG. 9B shows a top view of a deformed feminine hygiene pad worn by a 24 BMI consumer.
Figure 9C:
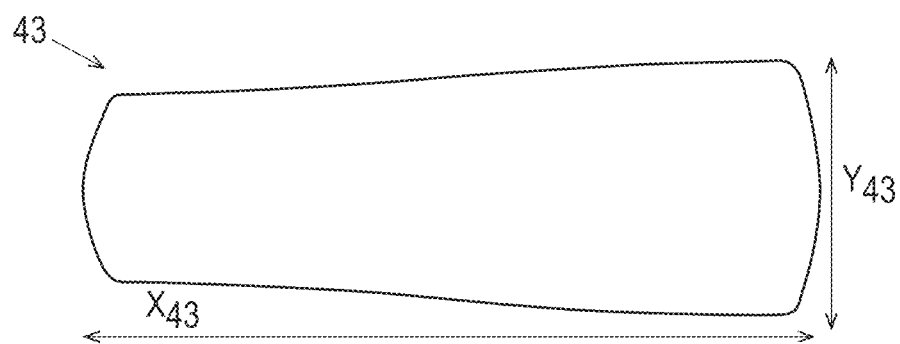
FIG. 9C shows a top view of an unworn, un-deformed feminine hygiene pad.

FIG. 8A depicts an approximated area 1130A on the coronal plane when viewing the coronal plane from the anterior portion into the posterior portion of the body. The approximated area 1130A shown is that for a high BMI wearer, e.g. 35. The area 1130A is defined by an intersection 1110A between a body torso 1120 and an inner thigh 1100A, an intersection 1110B between the body torso 1120 and an inner thigh 1100B and a transverse plane 1150A extending through the gluteal sulcus. As depicted, the area 1130A may be approximated by an inverted trapezoid. As BMI decreases, angles at the intersections 1110A and 1110B increase. In FIG. 8B, an approximated area 1130B for a lower BMI wearer, e.g. 15, is depicted. As shown, a transverse plane 1150B extending through the gluteal sulcus is much close to the torso 1120 than of FIG. 8A. The transverse planes 1150A and 1150B represent relative spacing of the panty to the torso. As depicted, the transverse plane 1150B is much close to the torso 1120 than the transverse plane 1150A. Accordingly, the approximated area 1130B With increased BMI, this reduced area results in the pad being compressed between the thighs in one or more of the X, Y, and Z directions, as shown in FIGS. 9A-9C, thereby reducing the projected area to the surface of the body, regardless of the starting surface area of the pad. FIG. 9A shows a top view of a deformed feminine hygiene pad 41 worn by a consumer having a BMI of 34. FIG. 9B shows a top view of a deformed feminine hygiene pad 42 worn by a consumer having a BMI of 24. FIG. 9C shows a top view of an unworn, un-deformed feminine hygiene pad 43. Each of the pads have an X direction length and a Y direction width. As shown, the Y direction width varies along the X direction length of each of the pads. Additionally, as depicted in FIGS. 9A and 9B, the Y direction width varies along the X direction as a function of BMI. Namely, deformation increases (Y direction width decreases in certain areas) as BMI increases. This deformation ultimately reduces the pad surface area available to contact the body and prevent spreading of fluid as described previously.

Figure 10A:
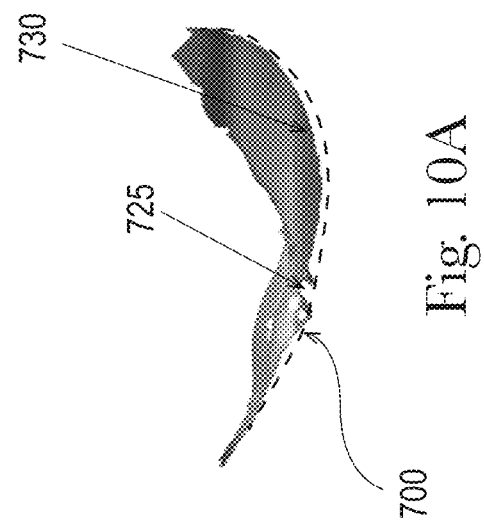
FIGS. 10A and 10B illustrate the body/panty interfaces of two different BMI women, e.g. 24 BMI and 34 BMI, respectively viewed from the sagittal plane.
Figure 10B:
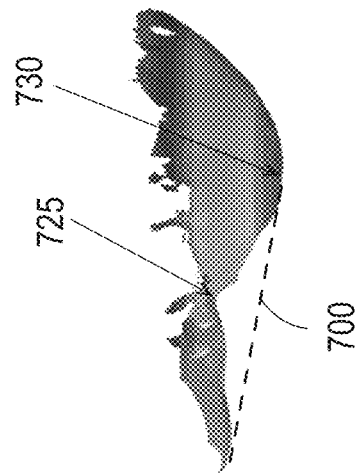
Figure 11A:
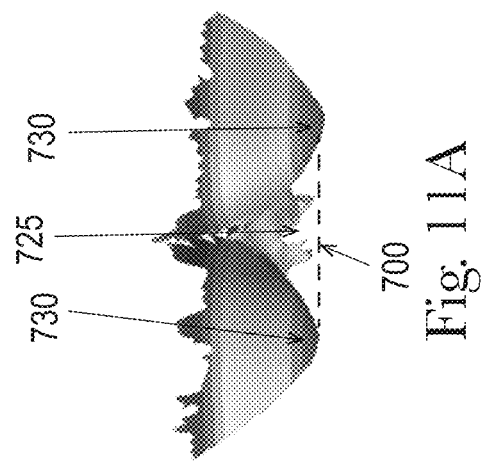
FIGS. 11A-11B illustrate the body/panty interfaces of two different BMI women, e.g. 24 BMI and 34 BMI, respectively viewed from the coronal plane.
Figure 11B:
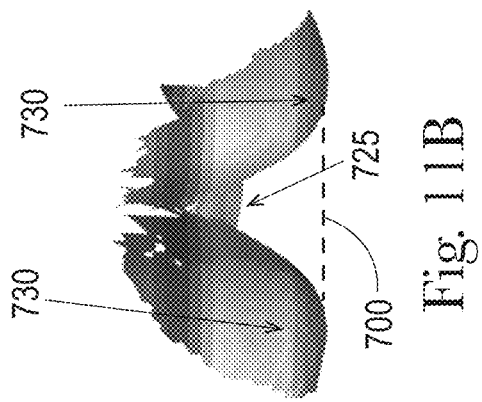
Figure 12A:
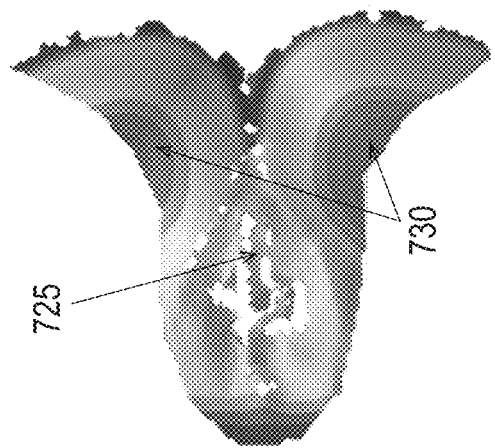
FIGS. 12A-12B show topographical surface maps of two different BMI women, e.g. 24 BMI and 34 BMI, respectively viewed from the transverse plane B-B from FIG. 2.
Figure 12B:
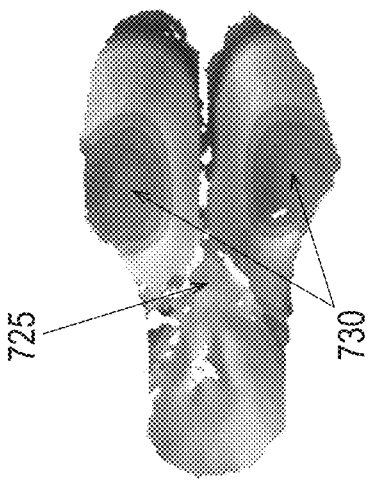

A new insight is that there exists a physical gap (a "panty-body void") between the body-facing surface of the panty (and an adult absorbent article that is adhered to that panty) and the center of the vaginal opening 725, as shown in FIGS. 10A-12B. The images shown were obtained via scans of test participants using a 3D scanner, e.g. Artec 3D Scanner manufactured by the Artec Group. The body/panty interface of a normal BMI woman (BMI of 24) versus that of a higher-BMI woman (BMI of 34) is illustrated in FIGS. 10A through 12B. As shown in FIG. 10A, a panty 700 for a wearer having a BMI of 24 follows the contour of the body 730 and is close to the vaginal opening 725. The surface of the panty conforms through the vulva region for the smaller woman (e.g., FIG. 10A). In contrast, the panty 700 tends to tent across the vulva region and vaginal opening 725 for the larger woman (e.g., FIG. 10B). As such, the panty 700 is much further away from the vaginal opening for the 34 BMI wearer. FIGS. 11A and 11B, for the 24 BMI and 34 BMI wearers, respectively, corroborate the illustrations in FIGS. 10A and 10B. Namely, the panty 700 is more proximate to the vaginal opening 725 for the 24 BMI wearer than the panty 700 of the 34 BMI wearer. FIGS. 12A-and 12B show topographical surface maps of the lower pelvic region bottom views) of a 24 BMI woman and a 34 BMI woman.

Most feminine pads are adhered to the panty of the wearer during use. As such, the presence of the panty-body void between the panty and the vaginal opening 725 will create a similar pad-body void. And, because the vaginal opening 725 is not in contact with the pad, this will create a performance outage. Lacking intimate contact, menses and urine tend to run along the body (i.e., they don't "drip" straight into the absorbent article) until they come into contact with either absorbent article or panty. This results in greater body soiling and a higher probability of garment soiling as depicted in FIGS. 1A-1C. Simply using a thicker pad and/or a longer pad will not address this outage because regardless of the length of the pad, the top surface of the pad will still tent across the vaginal opening for a larger BMI woman.

A one-size-fits-all approach would be insufficient since too much added caliper in a pad for smaller women will likely generate comfort concerns. However, a thinner caliper pad, as described above, may lead to performance outages for larger BMI women. The present invention solves this problem by creating an array of adult absorbent articles having characteristics and/or features designed to fill in the panty-body void, which in turn reduces spreading and which can accommodate lower BMI women. Now, a product array which accommodates various BMI women is achievable wherein each product within that array is designed for a different BMI range.

Figure 13A:
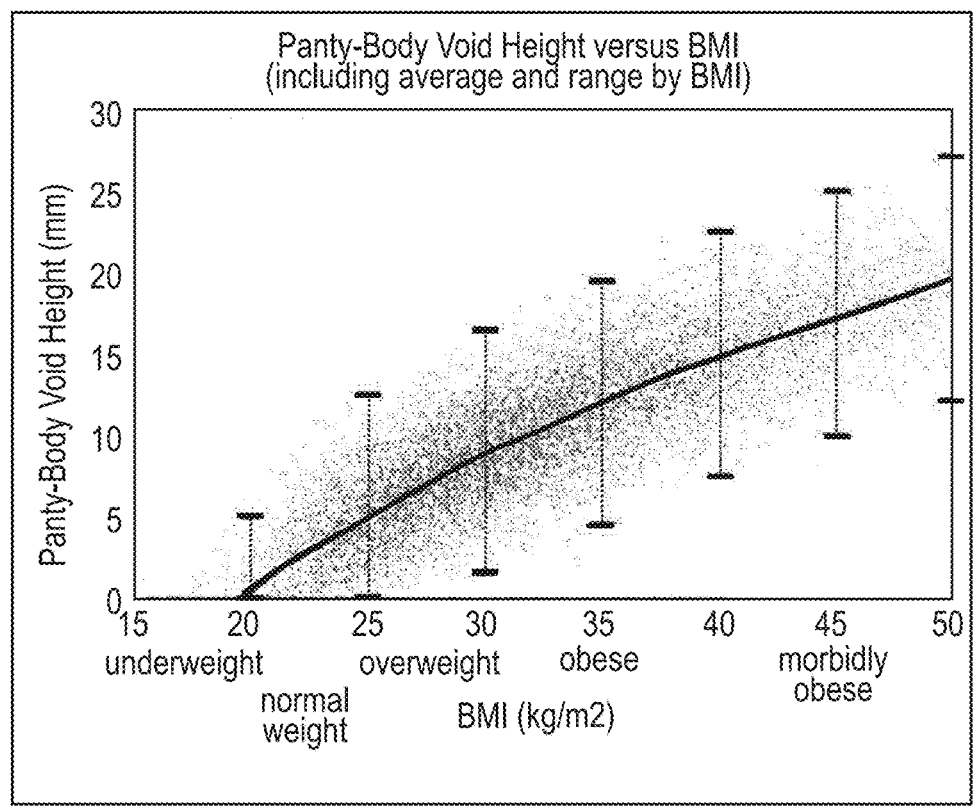
FIGS. 13A and 13B show how the probability and distance of the panty-body void height increases as BMI increases.
Figure 13B:
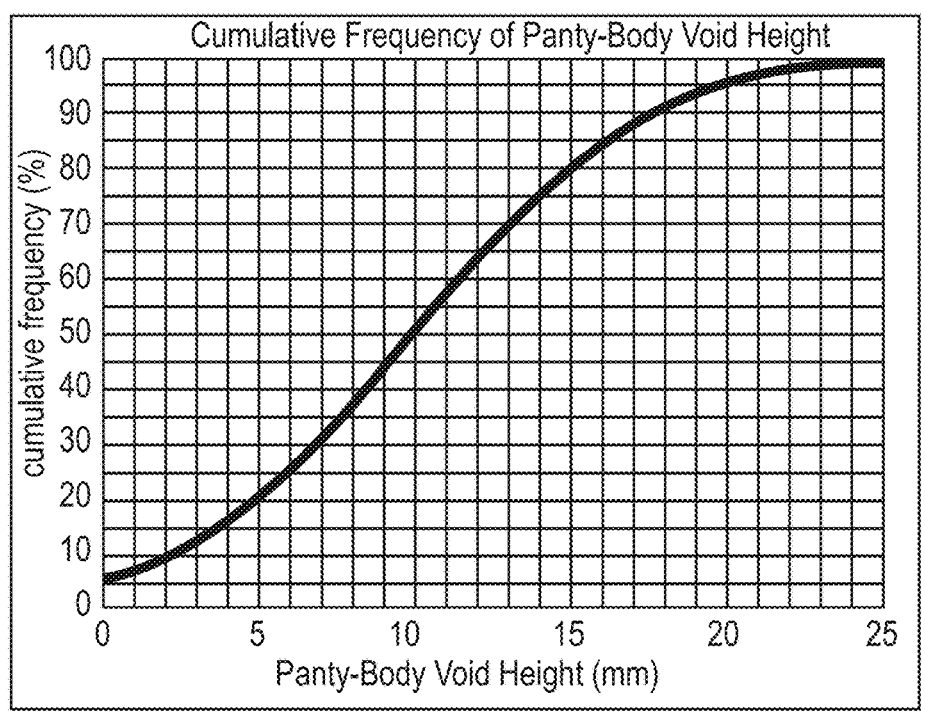

FIGS. 13A and 13B show how the panty-body void height increases as a function of BMI increase and the cumulative frequency of panty-body void height, respectively. In addition to the panty-body void height, the panty-body void width and the panty-body void length are also functions of BMI. Table 1 provides ranges with regard to each of the above. Going through the full range of BMI wearers, the panty-body void can be from about 0 cm to about 25 cm in length, from about 1 cm to about 4 cm in width, and from about 0 cm to about 3 cm in height. As shown in Table 1 below, the average dimensions of the panty-body void volume are all BMI dependent. The shape of the volume becomes higher and narrower as BMI increases. For example, the panty-body void volume for a normal BMI woman may be about the size of a golf ball, while the panty-body void volume for a morbidly obese woman may be about the size of an apple. This panty-body void is present with a majority of panties on the market; however, it is known that thongs, menstrual shorts, or the like may reduce the volume of the panty-body void.

TABLE 1

| Consumer Classification | Underweight | Normal | Overweight | Obese | Morbidly Obese |
| --- | --- | --- | --- | --- | --- |
| BMI Range | <20 | 20-25 | 25-30 | 30-40 | >40 |
| Panty-Body Void Height | 0 mm-5 mm | 0 mm-10 mm | 0 mm-15 mm | 5 mm-20 mm | 10 mm-30 mm |
| Panty-Body Void Length | 0 cm-10 cm | 0 cm-15 cm | 2 cm-20 cm | 5 cm-25 cm | 10 cm-25 cm |
| Panty-Body Void Width at Panty | 4 cm-8 cm | 4 cm-7 cm | 2 cm-6 cm | 0 cm-2 cm | 0 cm-1 cm |
| Panty-Body Void Width at Body | 3 cm-7 cm | 3 cm-6 cm | 2 cm-5 cm | 2 cm-3 cm | 2 cm-3 cm |
| Panty-Body Void Area at VO | 0 $cm^2$-4 $cm^2$ | 0 $cm^2$-6 $cm^2$ | 0 $cm^2$-8 $cm^2$ | 1 $cm^2$-6 $cm^2$ | 1 $cm^2$-6 $cm^2$ |
| Panty-Body Void Volume | 0 $cm^3$-30 $cm^3$ | 0 $cm^3$-75 $cm^3$ | 0 $cm^3$-100 $cm^3$ | 5 $cm^3$-120 $cm^3$ | 15 $cm^3$-150 $cm^3$ |

It is believed that filling this panty-body void can lead to better contact between the absorbent article and the body. This can reduce spreading (on the skin, on the pad), the probability of soiling, or leakage. In addition, this can increase comfort and security of the wearer. One way of accomplishing this is to develop an adult absorbent article comprising a physical feature to fill the volume of the void.

The adult absorbent article array may comprise one or more physical features which function to fill a wearer's panty-body void. This physical feature may be disposable or reusable. The physical feature may be manufactured integrally with an adult absorbent article, it may be packaged separately from an adult absorbent article as part of a kit, or the physical features may be sold separately from any adult absorbent article and be designed to work with a particular type or brand of adult absorbent articles, or further still, the physical features may be sold separately from any adult absorbent article and be designed to work with any type or brand of adult absorbent articles (e.g., a wearer who prefers U by Kotex® sanitary napkins can add an Always® physical feature to fill her panty-body void).

The physical feature may take the form of an additional absorbent core separate from the primary absorbent core, or the physical feature may be a primary core which is enhanced in a certain region. Still other embodiments are envisioned that comprise air bubbles (e.g, encapsulated by film), foam inserts, (e.g., may comprise adhesive), reusable pucks that can be placed under the adult absorbent article or between the pad and panty, elastics, fold up (e.g., tent across middle, along longitudinal axis) portions, pop up (e.g., from the backsheet to the topsheet), or other mechanics.

The physical feature may comprise one or more characteristics which make the physical feature appropriate for a particular wearer's BMI and/or panty-void volume. For instance, footprint, body-contact surface area, height, width, length, caliper, material(s) of construction, shape, fluid handling properties, permeability, hydrophobicity, color signals, acquisition speed, compressibility, recovery. All of these may relate to the physical feature itself or the physical feature as compared to the rest of the absorbent article. In addition, the physical feature may have different characteristics at different points in time, for instance, the feature may have a first height as packaged and a second height in use. These characteristics may be wearer-activated or altered prior to use, e.g., if an adult absorbent article is packaged in a substantially flat position, yet can be manipulated to have an increased caliper. The materials of construction may comprise any suitable absorbent materials known in the art. Some suitable examples include high internal phase emulsions, pulp, absorbent gelling material or superabsorbent material, any combination thereof or any of the materials disclosed below, or the like. The sides of the physical feature may be straight or tapered. The top of the physical feature may be flat, rounded, convex, concave, or the like. The footprint of the physical feature may be circular, oval, teardrop, triangular, etc.

Adult absorbent article arrays as disclosed herein may be manufactured by the same company on the same manufacturing line or on different manufacturing lines. Adult absorbent articles as disclosed herein may be sold in an array under the same brand (e.g., Depends, Always) and/or the same sub-brand name (e.g., Silhouette, Radiant).

Figure 14A:
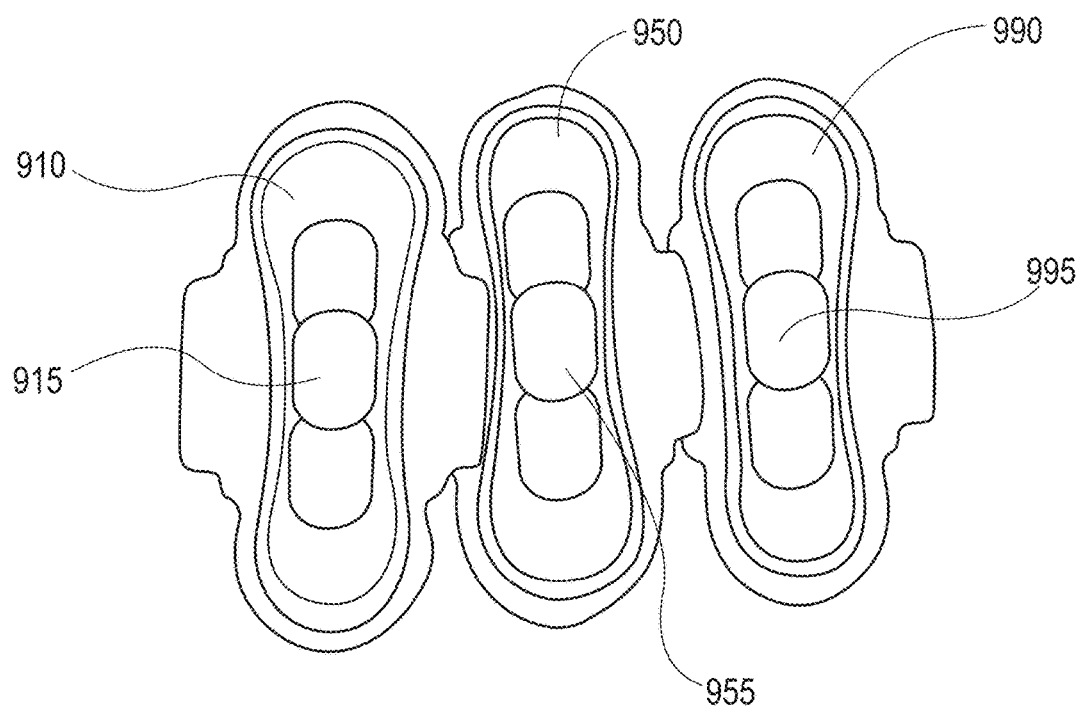
FIG. 14A shows a top view of an exemplary adult absorbent article array of the present invention.

An exemplary adult absorbent article array, comprising a first pad 910, a second pad 950, and a third pad 990, is shown in FIGS. 14A (top view) and 14B (perspective view). The pads in this array are labeled "size S," "size M," and "size L" for small, medium, and large options. This is one way of communicating to wearers that the product is customized based on their BMI. For example, the small size may be intended for wearers having a BMI under about 25, the medium size may be intended for wearers having a BMI from about 25-30, and the large size may be intended for wearers having a BMI above about 30. In another embodiment, an array may comprise a fourth size, extra-large ("XL") intended for wearers having a BMI above 40.

As shown, the first pad 910 may comprise a first physical feature 915 to address the panty-body void and be intended for wearers with a lower BMI. The second pad 950 may comprise a second physical feature 955 addressing the panty-body void of those wearers with a higher BMI than those intended wearers of the first pad 910. The third pad 990 may comprise a third physical feature 995 addressing the panty-body void of those wearers with a higher BMI than those intended wearers of the first pad 910 and of the second pad 950.

The first physical feature 915, the second physical feature 955, and the third physical feature 995 may be positioned on their respective pads such that each of the physical features lines up with the vaginal opening when in use. Additionally, the first physical feature 915, the second physical feature 955, and the third physical feature 995 can be different. With regard to the height (see callout H2 in FIG. 15C), length (see callout L2 in FIG. 15C), and/or width (see callout W2 in FIG. 15B) the third physical feature 995 may have a greater height, length, and/or width than that of the second physical feature 955. Similarly, the second physical feature 955 may have a greater height, length, and/or width than that of the first physical feature 915. Still in some executions, the third physical feature 995 has a greater height than that of the second physical feature 955 but has a length and/or width which is equal to or less than that of the second physical feature 955. Similarly, in some executions, the second physical feature 955 has a greater height than that of the first physical feature 915 but has a length and/or width which is equal to or less than that of the first physical feature 915.

Additionally, embodiments are contemplated where the second pad 950 and third pad 995 have a physical feature as described herein, but the first pad 910 does not have a physical feature 915 since it may not be required for intended wearer's BMI. Accordingly, the present invention envisions arrays in which two or more products in the array have a feature designed to fill the panty-body void. This may be a common feature or the array may comprise two or more different features—whatever works best to fill the panty-body voids of the intended wearers.

Figure 20:
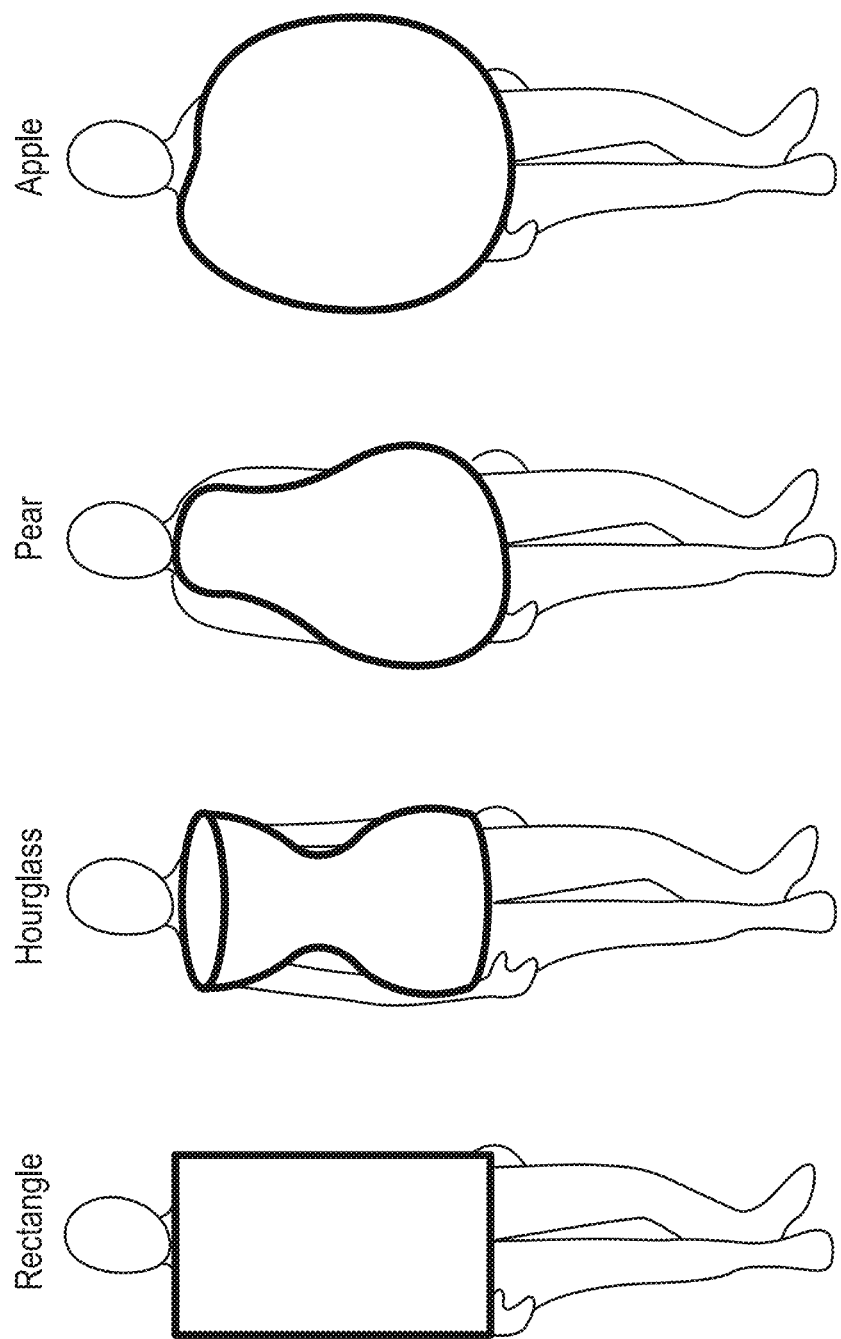
FIG. 20 illustrates a variety of specific shapes that may exist within each BMI class.

FIG. 20 illustrates a variety of specific shapes that may exist within each BMI class: rectangle, hourglass, pear, and apple. The higher her BMI, the further to the right a women typically is on this body shape scale. The prevalence of these shapes differs among BMI ranges, for instance, higher BMI women have a higher probability of being apple or pear shaped. Adult absorbent articles may be marketed to women of a particular body shape, such as apple, rather than focusing on exact BMI values (which may be off-putting to a consumer), in order to match a wearer with the article that will best fill her panty-body void.

As mentioned above, the physical features comprise characteristics which tailor the feature to the targeted BMI range. The array of FIGS. 14A and 14B utilize strategic caliper as a characteristic of the physical feature, which adds a z-directional component only to a specific region within the overall adult absorbent article footprint, wherein the height of this z-directional physical feature increases as targeted BMI range increases.

Figure 15A:
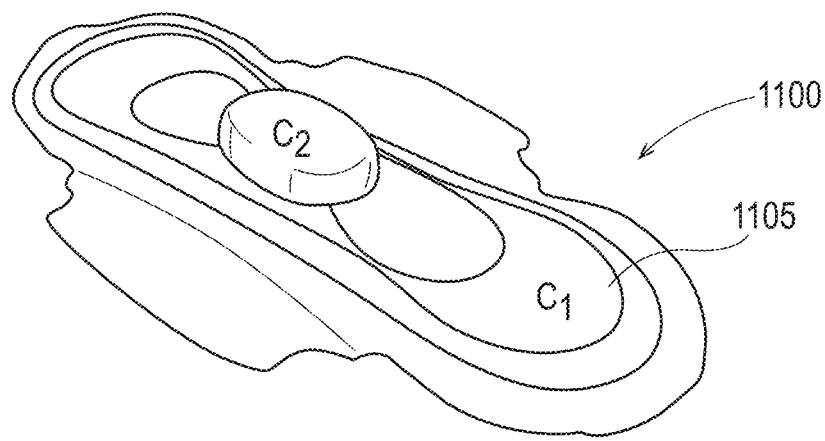
FIG. 15A shows an exemplary adult absorbent article in the form of a pad.
Figure 15B:
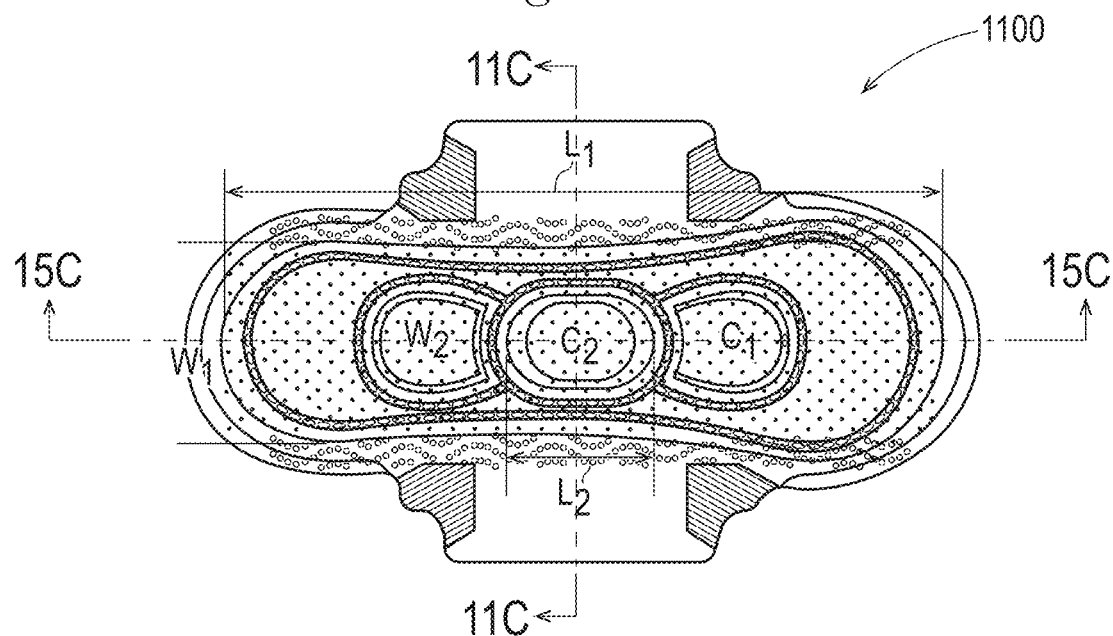
FIG. 15B is a top view schematic of the pad shown in FIG. 15A.
Figure 15C:
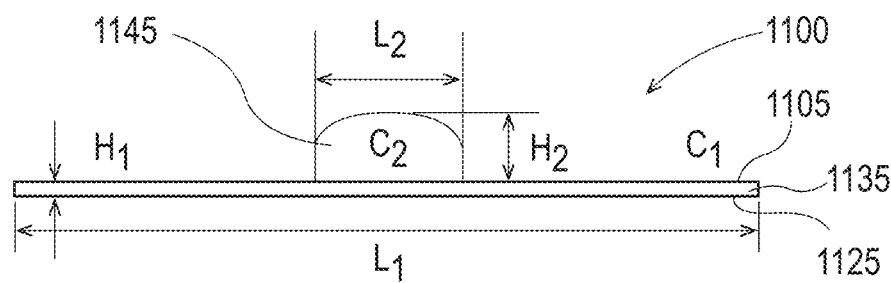
FIG. 15C is a cross-section diagram as taken through line 15C-15C of FIG. 15B.

An exemplary adult absorbent article in the form of a pad 1100 is shown in FIG. 15A. A top view schematic of the pad is shown in FIG. 15B. A cross-section of the pad 1100 is shown in FIG. 15C as taken through line 15C-15C in FIG. 15B. Pad 1100 is shown having a topsheet 1105, an opposing backsheet 1125, and a first absorbent core 1135 disposed therebetween. The absorbent core 1135 may comprise one or more layers as discussed hereafter. As shown, in some embodiments, the pad 1100 comprises the first absorbent core 1135 and a physical feature 1145 which can be a second absorbent core, in some embodiments. The first absorbent core 1135 has a length L1, a width W1, and a height HE In some embodiments, the absorbent articles are very thin (H1); for example, 0.5-5 millimeters, 1-4 millimeters, or 1.5-3.5 millimeters in caliper in regions excluding the physical feature(s) 1145, e.g. second absorbent core. The physical feature 1145 has a length L2, a width W2, and a height H2.

FIGS. 15A, 15B and 15C describe one embodiment of an array out of several possible array combinations disclosed in Table 2 additional combinations are contemplated. The dimension $W_1$ is measured at the narrowest portion of the pad, at the location where the pad is adhered to the center of the panty at the center of the crotch (the narrowest lateral spacing between the legs).

TABLE 2

| Product Size | S | M | L | XL |
|---|---|---|---|---|
| BMI Target Range | <25 | 25-30 | 30-40 | >40 |
| Body Shape Target | rectangle | hourglass | pear | apple |
| $H_2$ | 0 | 10 mm | 20 mm | 30 mm |
| $L_2$ | n/a | 7 cm | 15 cm | 20 cm |
| $W_2$ | n/a | 6 cm | 4 cm | 2 cm |
| $H_1$ | 5 mm | 5 mm | 5 mm | 5 mm |
| $L_1$ | 259 mm | 259 mm | 259 mm | 259 mm |
| $W_1$ | 60 mm | 60 mm | 50 mm | 40 mm |

$H_2$ increases as size increase due to the increase in panty-body void height as BMI increases. $W_1$ decreases as sizes increases due to the reduced spacing between the legs at the panty surface as BMI increases (See FIG. 3-5). W2 decreases as size increases due to the reduced width of the panty-body void volume as BMI increases.

Some embodiments are contemplated where an array of products comprise multiple sizes to accommodate multiple BMI wearers. For example, an array may comprise a first size for those wearers having a BMI of 25 or less, a second size for those wearers having a BMI of between about 25 to 30, a third size for wearers having a BMI of between about 30 to 40, and a fourth size for wearers having a BMI of greater than 40. The physical feature, described in FIGS. 14A and 14B may have varying lengths (L2 shown in FIG. 15C), widths (W2 shown in FIG. 15B) and/or heights (H2 shown in FIG. 15C). In some constructions, the first size may not include a physical feature while the second size, third size, and fourth sizes do comprise a physical feature. In such arrays, a ratio of heights of the physical features of the third size to the second size may be from about 5 to 1 to about 1.3 to 1. Additionally, in such constructions, a ratio of heights between the physical features of the fourth size to the third size may be about 2 to 1 to about 1.3 to 1. For such arrays, the first size may comprise a physical feature. In such constructions, in addition to the foregoing ratios between the third and second and fourth and third sizes, a ratio of height of the physical feature of the second size to the first size may be from about 10:1 to about 1.5 to 1.

A ratio of lengths of the physical features of the third size to the second size may be from about 2.5 to 1 to about 1.25 to 1. A ratio of lengths of the physical features of the fourth size to the third size may be from about 2 to 1 to about 1 to 1. And, for those arrays wherein the first size comprises a physical feature, a ratio of lengths of the physical features of the second size to the first size may be from about 2 to 1 to about 1.25 to 1.

A ratio of widths of the physical features of the second size to the third size may be from about 1 to 1 to about 5 to 3. A ratio of width of the physical features of the third size to the fourth size may be about 1 to 1. And for those arrays where the first size comprises a physical feature, a ratio of widths of the physical feature of the first size to the second size may be from about 3 to 2 to about 6 to 5.

A ratio of volumes of the physical features of the fourth size to the third size may be from about 3 to 1 to about 5 to 4. A ratio of volumes of the physical features of the third size to the second size may be from about 5 to 1 to about 6 to 5. And for those arrays where the first size comprises a physical feature, a ratio of volumes of the physical feature of the second size to the first size may be from about 1 to 1 to about 3 to 1.

The array described above comprising four sizes may vary the physical feature height, length, width, and/or volume.

Arrays are also contemplated where five sizes are offered. For example, an array may comprise a first size for those wearers having a BMI of 20 or less, a second size for those wearers having a BMI of between about 20 to 25, a third size for wearers having a BMI of between about 25 to 30, a fourth size for wearers having a BMI of between 30 to 40, and a fifth size for wearers having a BMI of greater than 40. Similar to the above, in some constructions, the first size may not include a physical feature while the second size, third size, fourth size, and fifth size do comprise a physical feature. In such arrays, a ratio of heights of the physical features of the third size to the second size may be from about 1 to 1 to about 3 to 2. A ratio of heights between the physical features of the fourth size to the third size may be about 5 to 1 to about 4 to 3. For such arrays, the first size may comprise a physical feature. A ratio of heights between the physical features of the fifth size and the fourth size may be between about 2 to 1 to about 3 to 2. In such constructions, in addition to the foregoing ratios between the third and second and fourth and third sizes, a ratio of height of the physical feature of the second size to the first size may be from about 1:1 to about 2 to 1.

A ratio of lengths of the physical features of the third size to the second size may be from about 2 to 1 to about 4 to 3. A ratio of lengths of the physical features of the fourth size to the third size may be from about 2.5 to 1 to about 1.25 to 1. A ratio of lengths of the physical features of the fifth size to the fourth size may be between about 2 to 1 to about 1 to 1. And, for those arrays wherein the first size comprises a physical feature, a ratio of lengths of the physical features of the second size to the first size may be from about 1 to 1 to about 1.5 to 1.

A ratio of widths of the physical features of the second size to the third size may be from about 1.5 to 1 to about 1.2 to 1. A ratio of width of the physical features of the third size to the fourth size may be about 1 to 1 to about 1.6 to 1. A ratio of width of the physical features of the fourth size to the fifth size may be about 1 to 1. And for those arrays where the first size comprises a physical feature, a ratio of widths of the physical feature of the first size to the second size may be from about 1 to 1 to about 7 to 6.

A ratio of volumes of the physical features of the third size to the second size can be between about 1 to 1 to about 1.3 to 1. A ratio of volumes of the physical features of the fourth size to the third size may be from about 5 to 1 to about 6 to 5. A ratio of volumes of the physical features of fifth size to the fourth size may be from about 3 to 1 to about 1.25 to 1. And for those arrays where the first size comprises a physical feature, a ratio of volumes of the physical feature of the second size to the first size may be from about 1 to 1 to about 2.5 to 1. Arrays are also contemplated where three sizes are offered. For example, an array may comprise a first size for those wearers having a BMI of 25 or less, a second size for those wearers having a BMI of between about 25 to 40, and a third size for wearers having a BMI of greater than 40. Similar to the above, in some arrays, the first size may not include a physical feature while the second size and third size do comprise a physical feature. In such arrays, a ratio of heights of the physical features of the third size to the second size may be from about 10 to 1 to about 2 to 1. For such arrays, the first size may comprise a physical feature. In such constructions, in addition to the foregoing ratios between the third and second sizes, a ratio of height of the physical feature of the second size to the first size may be from about 5:1 to about 4 to 1.

A ratio of lengths of the physical features of the third size to the second size may be from about 5 to 1 to about 1.25 to 1. And, for those arrays wherein the first size comprises a physical feature, a ratio of lengths of the physical features of the second size to the first size may be from about 5 to 1 to about 2.5 to 1.

A ratio of widths of the physical features of the second size to the third size may be from about 1.5 to 1 to about 2 to 1. And for those arrays where the first size comprises a physical feature, a ratio of widths of the physical feature of the first size to the second size may be from about 1.5 to 1 to about 2.3 to 1.

A ratio of volumes of the physical features of the third size to the second size can be between about 15 to 1 to about 1.5 to 1. And for those arrays where the first size comprises a physical feature, a ratio of volumes of the physical feature of the second size to the first size may be from about 5 to 1 to about 4 to 1.

Still in some executions, the physical feature described herein may comprise a ratio of length to height of about 250 to 1, 200 to 1, 150 to 1, 100 to 1, 50 to 1, or 25 to 1. Similarly, physical features described herein may comprise a ratio of width to height of about 70 to 1, 60 to 1, 50 to 1, 25 to 1, 10 to 1,6 to 1,or 5 to 1.

Embodiments are contemplated where the height of the physical features of those sizes associated with larger BMI wearers increases with increasing BMI while the width of the physical feature decreases with increasing BMI. Also, embodiments are contemplated where the width of the primary core (W1 shown in FIG. 15B) decreases with increasing BMI. For example, a feminine care article of a size associated with a BMI larger than 24 may have a lower width (W1) than that of a feminine care article of a size associated with a BMI of less than 24. Similar configurations can be made with regard to those size associated with a BMI of greater than 30, greater than 34, greater than 40, greater than 45, etc.

Figure 16A:
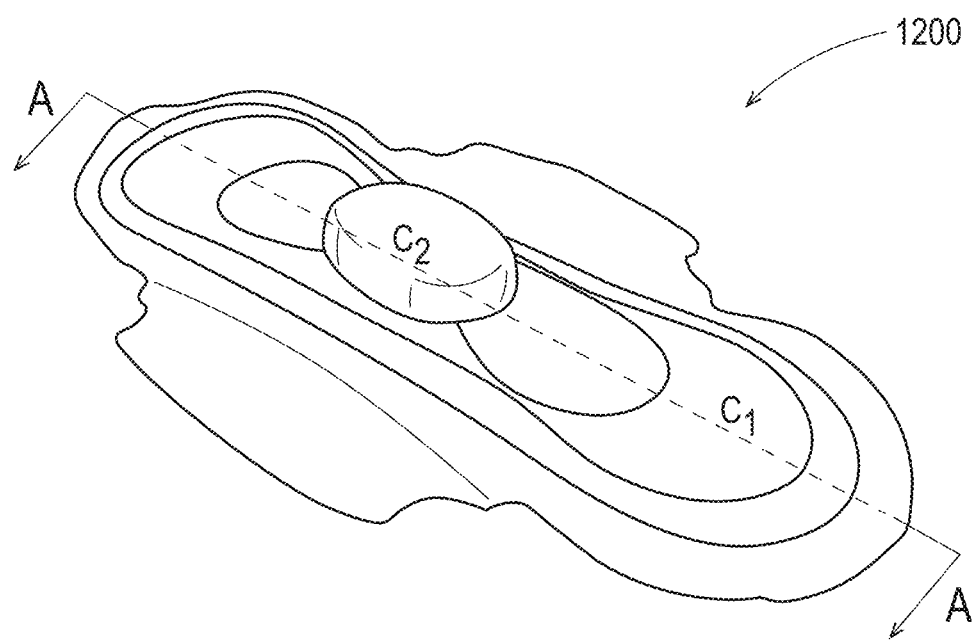
FIG. 16A is an additional exemplary embodiment of an adult absorbent article comprising a physical feature.
Figure 16B:
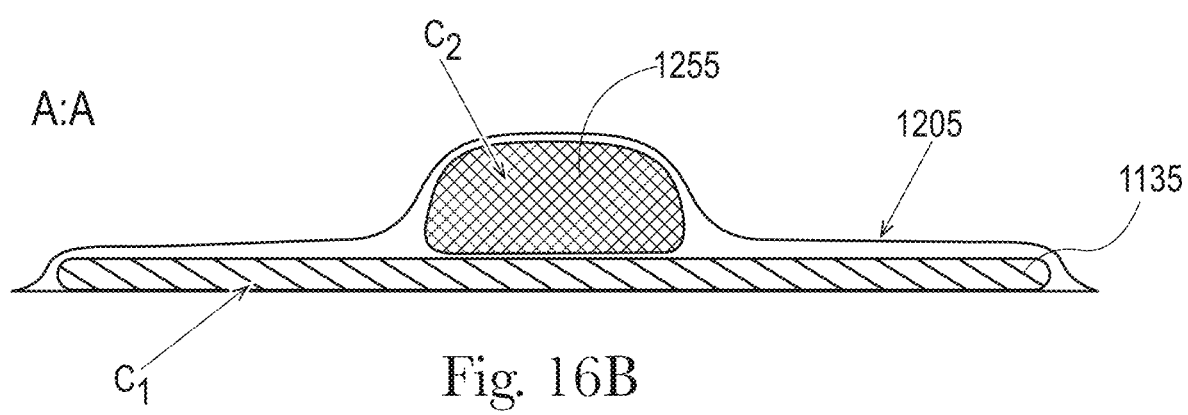
FIG. 16B is a cross-section view of the article of FIG. 16A, taken along the line A-A.

Additional exemplary embodiments of feminine care articles comprising physical features are illustrated in FIGS. 16A-19B. In these figures, the first absorbent core 1135 is the primary core of the adult absorbent article. FIG. 16A is an additional exemplary embodiment of an adult absorbent article 1200 comprising a physical feature 1255 FIG. 16B is a cross-section view of the article 1200 of FIG. 16A, taken along the line A-A. The physical feature 1255 is a core integral with the article 1200. It is covered by a topsheet 1205 and comprises absorbent material.

Absorbent material refers to liquid absorbent materials such as for example soft materials providing a rather fluffy structure with empty space, such as comminuted wood pulp, creped cellulose wadding, chemically stiffened, modified or cross-linked cellulosic fibers all of which are herein referred to as "airfelt". Absorbent material also refers to superabsorbent polymer material (SAP), such as super absorbent polymer polymers, fibers or foams and mixtures of superabsorbent polymer material with airfelt.

Figure 17A:
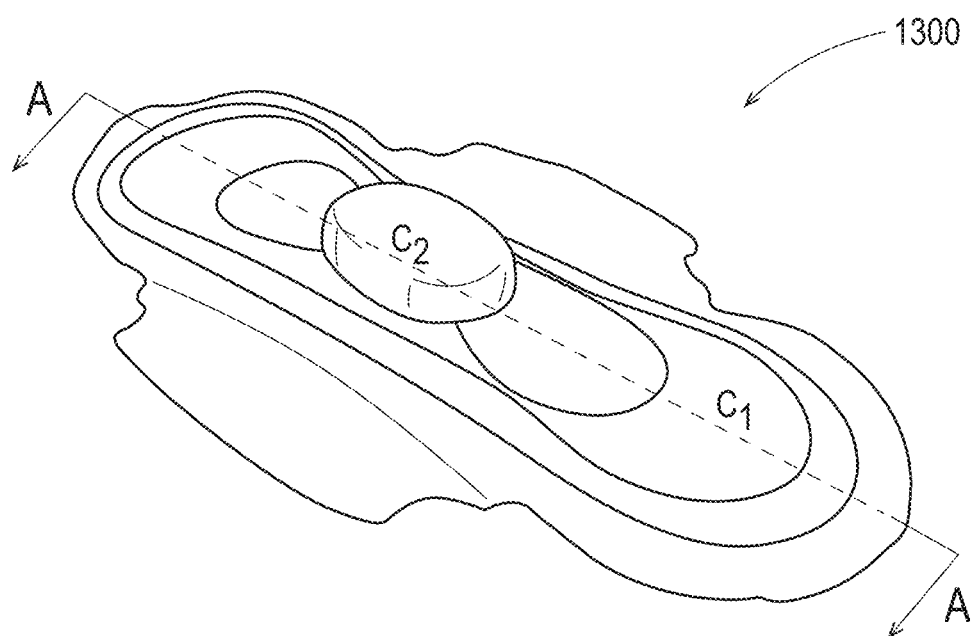
FIG. 17A is an additional exemplary embodiment of an adult absorbent article comprising a physical feature.
Figure 17B:
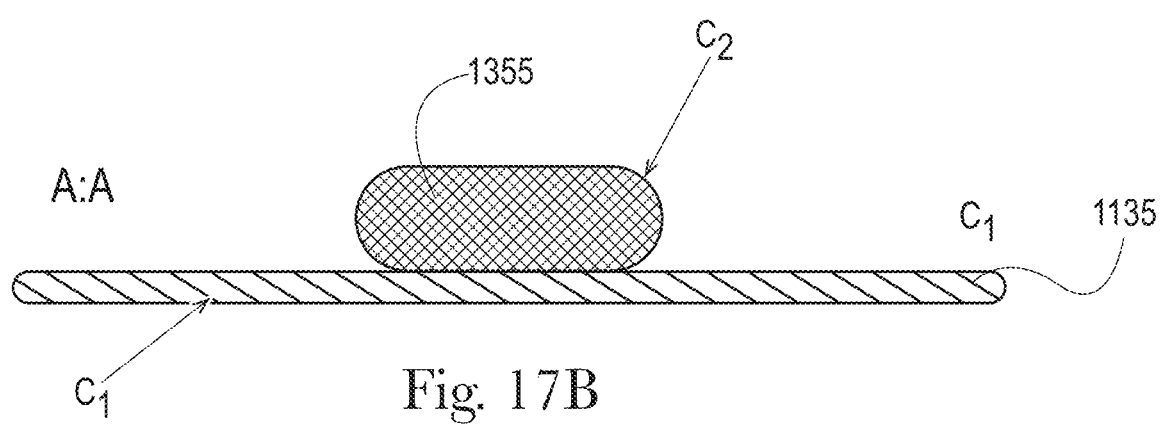
FIG. 17B is a cross-section view of the article of FIG. 17A, taken along the line A-A.

FIG. 17A is an additional exemplary embodiment of an adult absorbent article 1300 comprising a physical feature 1355. FIG. 17B is a cross-section view of the article 1300 of FIG. 17A, taken along the line A-A. The physical feature 1355 is a separate structure which may be attached and removed from the article. Any suitable attachment mechanism can be utilized. Some suitable examples include adhesive or a hook and loop structure, e.g., velcro. However, with such constructions, the physical feature 1355 should maintain sufficient liquid communication with the first absorbent core 1135 to reduce the likelihood of leakage.

Figure 14B:
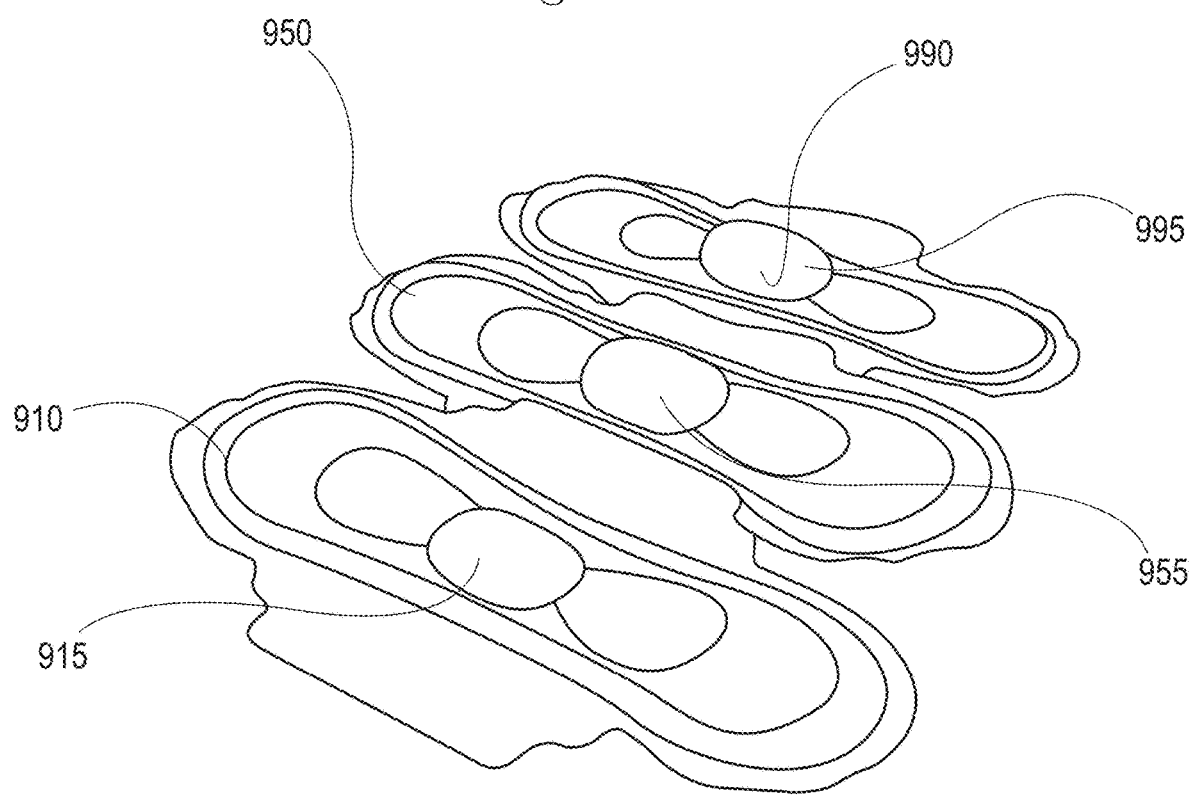
FIG. 14B shows a perspective view of the exemplary adult absorbent article array of FIG. 14A.
Figure 18A:
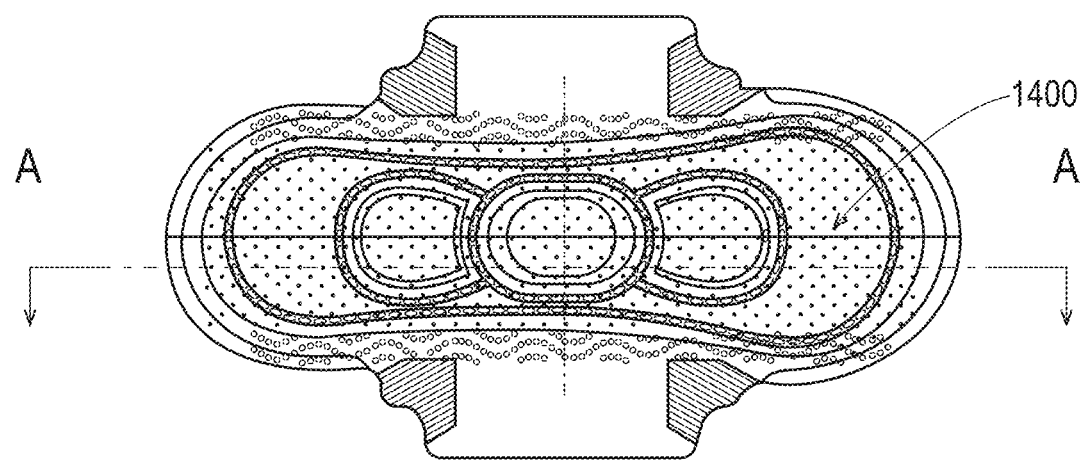
FIG. 18A is an additional exemplary embodiment of an adult absorbent article comprising a physical feature.
Figure 18B:
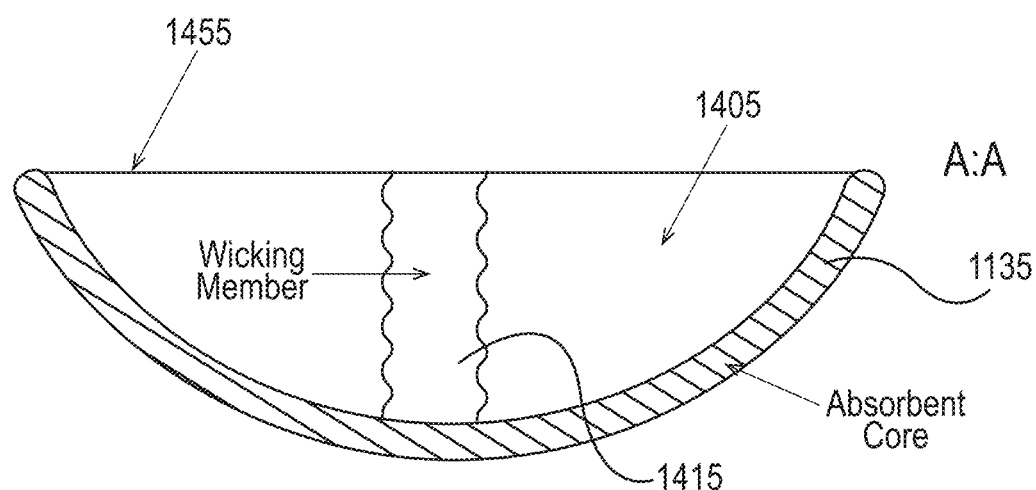
FIG. 18B is a cross-section view of the article of FIG. 18A, taken along the line A-A.

FIG. 18A is an additional exemplary embodiment of an adult absorbent article 1400 comprising a physical feature 1455. FIG. 14B is a cross-section view of the article 1400 of FIG. 18A, taken along the line A-A. The physical feature 1455 is elastic, preferably a pre-stretched elastic strand that extends longitudinally under a topsheet 1405. The elastic causes the topsheet 1405 to tent in use and thus creates conformity to the vaginal opening. A wicking member 1415 may be present (e.g., an absorbent material) to create a continuous pathway between the topsheet and absorbent core to transport fluid through the topsheet 1405 to the absorbent core 1135. The wicking member 1415 may be adhered to the underside of the topsheet 1405 via any suitable method, e.g. adhesive or thermal bond. The wicking member 1415 may also be adhered to the absorbent core 1135 via adhesive or a thermal bond . . . 1435.

Figure 19A:
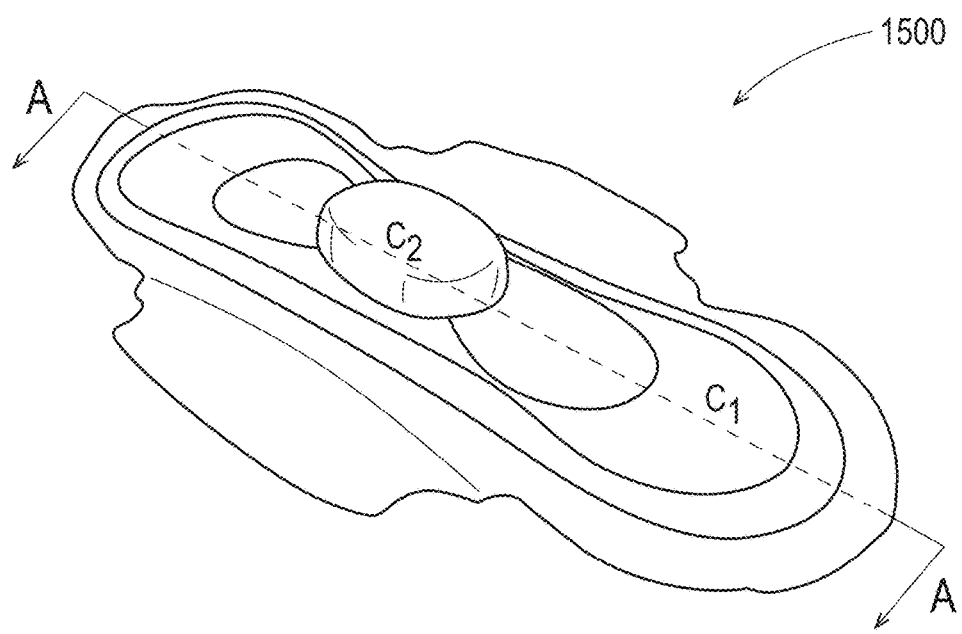
FIG. 19A is an additional exemplary embodiment of an adult absorbent article comprising a physical feature.
Figure 19B:
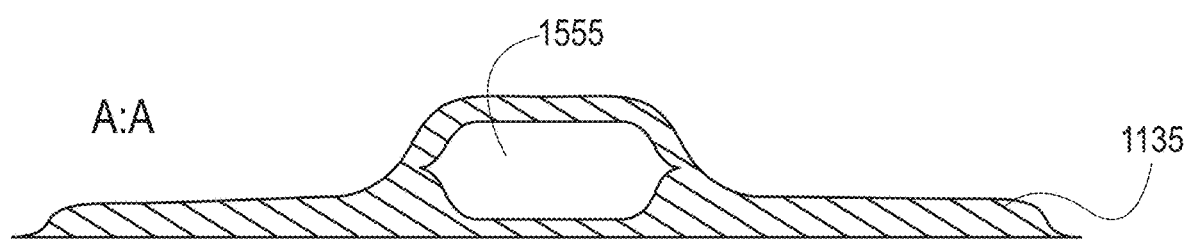
FIG. 19B is a cross-section view of the article of FIG. 19A, taken along the line A-A.

FIG. 19A is an additional exemplary embodiment of an adult absorbent article 1500 comprising a physical feature 1555. FIG. 19B is a cross-section view of the article of FIG. 19A, taken along the line A-A. The physical feature 1555 is an encapsulated air bubble integral with the article 1500. It is air in a sealed film pocket which, in some embodiments may be covered by an absorbent material and a topsheet 1505. Any suitable absorbent material may be utilized.

Test Methods

There are many test methods which can provide insight into the characteristics of a physical feature as described herein. All measurements are conducted at 22° C.+/− 2° and 50% RH+/− 20%. Samples are conditioned for at least two hours prior to testing under the same conditions. Linear measurements are made with a device that is traceable to NIST or other standards organization. Each measurement below is to be conducted on 10 separate like specimens and the average of the 10 separate like specimens is considered to be the measurement for that specific specimen set.

1. Caliper, (z directional thickness of H1 and H2) is measured using a Digital Manual Fabric Thick Measuring equipment, e.g., Gester YG141N, or other height gauge device, e.g., Tormach Tool PN 31988. The thickness of H1 is measured by inserting the pad into the devise such that only H1 is captured within the device. The foot of the gauge device should brought into contact with the sample until the foot is visibly touching the sample. No additional pressure should be applied to the foot once the foot contacts the sample. H2 is measured by placing the pad into the device, such that both H1 and H2 are captured. The combined caliper of H1 and H2 are measured, and H2 is determined by subtracting the caliper of H1. All measurements are conducted with no added pressure.
2. Dimensions (W1, W2, L1, L2) are measured with a ruler, with each product laid flat in its relaxed state.

Pads that are intended to be worn in one's undergarments can employ fastening means, such as adhesive, for temporarily affixing the article to the undergarment. The shape of the adhesive area may be full coverage, or one or two or more strips of longitudinally oriented adhesive strips instead of full coverage. The adhesive strips may then be continuous or intermittent. For example, two longitudinally oriented strips, one on each side of the longitudinal axis, may be applied. The adhesive may be applied via direct slot coating application process or via a non-contact process. Mechanical adhesive means may be also provided, such as microscopic hooks placed on the backsheet and designed to attach to the fibers present in some undergarments, as in a hook-and-loop fastener.

The topsheet is typically the layer of the adult absorbent article that is oriented towards and contacts the body of the wearer, and is therefore the first layer to receive bodily exudates. The topsheet is normally made of a single layer, but may also comprise more than one layer (for example a central topsheet layer and two overlapping lateral stripes, as disclosed in WO93/09744 or EP766,953). The topsheet is normally liquid pervious. The term "liquid pervious" as used herein refers to components that allow liquids to pass therethrough without significantly retarding or obstructing the transmission of such liquids therethrough.

It is envisaged that any conventional topsheet materials may be used within the invention. Suitable topsheets may be made for example from nonwoven materials or perforated polyolefinic films. An exemplary topsheet suitable for use herein is a relatively hydrophobic 20 gsm spunbonded nonwoven web comprising bicomponent fibers of the sheath core type (PP/PE).

If desired, the topsheet may be treated with a surfactant to enhance liquid penetration to an underlying absorbent core. The surfactant is typically non-ionic and should be nonirritating to the skin. A surfactant density of about 0.01 milligrams per square centimeter of topsheet area is normally suitable. An exemplary surfactant is sold by the Glyco Chemical, Inc. of Greenwich, Connecticut as Pegosperse 200 ML. The topsheet may have a plurality of apertures or other structures to permit liquids deposited thereon to pass through to the absorbent core more quickly.

The general function of the backsheet is to prevent discharges absorbed by the core from escaping the sanitary napkin and soiling the wearer or their clothing. The backsheet may be made of any suitable material; in particular, any standard backsheet materials. These materials are generally flexible, liquid resistant, and liquid impervious. Exemplary backsheet materials include, but are not limited to, polyolefinic films or nonwoven webs. Nonwoven webs may be advantageous because they normally provide better breathability for the articles and may be cheaper than polyolefinic films. For example, a relatively hydrophobic 18 grams per square meter (gsm) spunbonded nonwoven web of 2 denier polypropylene fibers. The backsheet may also be a laminate as is known in the art.

The topsheet and the backsheet can be peripherally joined using known techniques such as heat embossing and ultrasonic bonding. The layers may also be glued to each other. The topsheet may be contiguous with the backsheet with these two layers forming the outer periphery of the article. The adult absorbent articles may comprise attached wings, integral wings, or no wings.

The adult absorbent articles contemplated by the present invention further comprise an absorbent core disposed between the topsheet and the backsheet. As used herein, the term "absorbent core" refers to a material or combination of materials suitable for absorbing, distributing, and storing fluids such as urine, blood, menses, and/or other body exudates. The absorbent core may or may not be affixed to the topsheet and backsheet.

The absorbent core can be made of any suitable materials. Nonlimiting examples of suitable liquid-absorbent materials include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; HIPE; absorbent sponges; synthetic staple fibers; peat moss; or any equivalent material; or combinations thereof. The absorbent core can comprise superabsorbent polymer (SAP), normally distributed within a matrix of cellulosic fibers, for example in order to reduce the thickness of the absorbent core.

The absorbent core can be unitary, or can be a laminate of two or more layers. For example, the core can comprise a fluid impermeable barrier layer (e.g., a PE Patch) on its backsheet-facing side to prevent fluids retained by the absorbent core from striking through the pantiliner and soiling adjacent garments. An exemplary PE patch is a 25 gsm poly film available from Britton Taco (UK) under trade name ST-012A-White. Further general information regarding absorbent cores can be found in prior patent publications, see for example PCT publications WO207662A1 and WO9119471.

The adult absorbent articles may be packaged in an un-folded state and without an optional individual wrapper feature. In alternative embodiments of the present invention, the articles can be folded (e.g., bi-folded or tri-folded) and/or packaged in individual wrappers. Such secondary packaging is known to the skilled artisan, and can be made out of flexible polymeric films or nonwovens. These individual wrappers can take on a variety of configurations, such as a pouch that can facilitate disposal of a soiled absorbent article. In still other embodiments, the physical feature may be packaged separately from the adult absorbent article, for example, a box of additional cores may be sold alongside sanitary napkins, wherein a user is instructed to place an additional core on top of a sanitary napkin to customize her panty-body fit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An array of adult absorbent articles, the array comprising:
   a. a first absorbent article comprising:
      i. a topsheet, a backsheet, and a first absorbent core, the first absorbent core having a first absorbent core length;
      ii. a first physical feature disposed between the first absorbent core and the topsheet; and
   b. a second absorbent article comprising;
      i. a topsheet, a backsheet, and a second absorbent core, the second absorbent core having a second absorbent core length;
      ii. a second physical feature disposed between the second absorbent core and the topsheet;
   wherein the first physical feature comprises a first characteristic based on a first body-mass index, wherein the first characteristic is a first length, wherein the first length is between 27 percent and 77 percent of the first absorbent core length, wherein the second physical feature comprises a second characteristic based on a second body-mass index, wherein the second characteristic is a second length, wherein the second length is between 27 percent and 77 percent of the second absorbent core length, wherein the first length is less than the second length; wherein the first physical feature comprises a convex portion oriented toward a first end of the first absorbent article or the second physical feature comprise a convex portion oriented toward a first end of the second absorbent article, and wherein the first absorbent article and the second absorbent article are manufactured by the same company.

2. The array of claim 1, wherein the first absorbent article and the second absorbent article share a common brand name or sub-brand name.

3. The array of claim 1, wherein the first body-mass index is less than the second body-mass index.

4. The array of claim 1, wherein the first physical feature and second physical feature are sized to substantially fill a particular panty-body void.

5. The array of claim 1, further comprising a third absorbent article comprising a topsheet, a backsheet, and a third absorbent core; wherein the third absorbent article does not comprise a third physical feature.

6. The array of claim 5, wherein the third absorbent article, the first absorbent article, and the second absorbent article share a common brand name or sub-brand name.

7. The array of claim 5, wherein the third absorbent article not comprising a third physical feature is based upon a third body-mass index.

8. The array of claim 7, wherein the third body-mass index is less than the first body-mass index and less than the second body-mass index.

9. The array of claim 5, wherein the first, second, and third absorbent articles are sanitary napkins.

10. The array of claim 1, wherein the first absorbent article and the second absorbent article are both sanitary napkins.

11. The array of claim 5, wherein the first absorbent article and the second absorbent article are both sanitary napkins and the third absorbent article is a pantiliner.

12. The array of claim 5, wherein the first, second, and third absorbent articles are selected from the group consisting of adult incontinence pads, adult incontinence liners, adult incontinence pants, sanitary pads, and sanitary pantiliners.

13. The array of claim 1, wherein the first absorbent article and the second absorbent article are both selected from the group consisting of adult incontinence pads, adult incontinence liners, adult incontinence pants, sanitary pads, and sanitary pantiliners.

14. An array of adult absorbent articles, the array comprising:
a first absorbent article in a first size having a topsheet, a backsheet, a first absorbent core disposed between the topsheet and the backsheet; and a first physical feature disposed between the first absorbent core and the topsheet, wherein the first absorbent core has a first absorbent core length and the first physical feature has a first length, wherein the first length is less than the first absorbent core length, and wherein the first physical feature is separate from the first absorbent core; and
a second absorbent article in a second size having a topsheet, a backsheet, and a second absorbent core and a second physical feature disposed between the absorbent core and the topsheet, wherein the second absorbent core has a second absorbent core length and the second physical feature has a second length, and wherein the second length is less than the second absorbent core length, and wherein the second physical features is separate from the second absorbent core; and
wherein each of the first physical feature comprises a height based on a first body-mass index and the second physical feature comprises a height based on a second body-mass index, wherein a ratio of the first physical feature height to the second physical feature height is between about 5 to 1 to about 1.5 to 1, and wherein the first physical feature has a convex portion oriented toward a first end of the first absorbent article and/or the second physical feature has a convex portion oriented toward a first end of the second absorbent article.

15. The array of adult absorbent articles of claim 14 further comprising a third absorbent article in a third size, wherein the third absorbent article does not comprise a physical feature.

16. The array of adult absorbent articles of claim 14 further comprising a third absorbent article in a third size, wherein the third absorbent article comprises a physical feature having a height, wherein a ratio of the third physical feature height to the second physical feature height is between about 5 to 1 to about 4 to 1.

17. The array of adult absorbent articles of claim 14, wherein a ratio of the first length to the second length is from about 2.5 to 1 to about 1.25 to 1.

18. The array of adult absorbent articles of claim 17, further comprising a third absorbent article having a third size, wherein the third absorbent article does not comprise a physical feature.

19. The array of adult absorbent articles of claim 17, further comprising a third absorbent article having a third size, wherein the third absorbent article comprises a physical feature having a third length, and wherein a ratio of the third length to the second length is from about 1.5 to 1 to about 1 to 1.

20. The array of adult absorbent articles of claim 14, wherein the first physical feature has a first height, wherein a ratio of the first length to the first height is from about 250 to 1 to about 2.5 to 1.

21. The array of adult absorbent articles of claim 20, wherein the second physical feature has a second height, wherein a ratio of the second length to the second height is from about 25 to 1 to about 30 to 1.

* * * * *